United States Patent
Shrestha et al.

(10) Patent No.: US 9,351,702 B2
(45) Date of Patent: May 31, 2016

(54) ULTRASONIC SCANNING PROBE WITH A TUNING FORK-TYPE OSCILLATOR AND FEEDBACK CONTROL THEREOF

(75) Inventors: Shailesh Shrestha, Bremen (DE); Ahsan Nawroj, Easton, PA (US); Yih-Choung Yu, Easton, PA (US); Marcos Sotomayor, New York, NY (US); Richard Koplin, New York, NY (US)

(73) Assignee: Noble Sensors, LLC, New York, NY (US)

( * ) Notice: Subject to any disclaimer, the term of this patent is extended or adjusted under 35 U.S.C. 154(b) by 184 days.

(21) Appl. No.: 13/443,136

(22) Filed: Apr. 10, 2012

(65) Prior Publication Data

US 2012/0236258 A1   Sep. 20, 2012

Related U.S. Application Data

(63) Continuation-in-part of application No. 12/643,186, filed on Dec. 21, 2009, now abandoned.

(60) Provisional application No. 61/149,057, filed on Feb. 2, 2009, provisional application No. 61/474,009, filed on Apr. 11, 2011, provisional application No. 61/513,731, filed on Aug. 1, 2011, provisional application No. 61/569,466, filed on Dec. 12, 2011.

(51) Int. Cl.
*A61B 3/10*    (2006.01)
*A61B 8/10*    (2006.01)
*A61B 8/00*    (2006.01)

(52) U.S. Cl.
CPC ... *A61B 8/10* (2013.01); *A61B 3/10* (2013.01); *A61B 8/4281* (2013.01); *A61B 8/4461* (2013.01); *A61B 8/4466* (2013.01); *A61B 8/546* (2013.01)

(58) Field of Classification Search
CPC .......... A61B 3/10; A61B 8/546; A61B 8/446
USPC ............ 73/634, 620, 626, 633, 635; 351/205
See application file for complete search history.

(56) References Cited

U.S. PATENT DOCUMENTS

| | | | |
|---|---|---|---|
| 3,990,300 A * | 11/1976 | Kossoff | 73/640 |
| 4,094,306 A * | 6/1978 | Kossoff | 73/607 |
| 4,104,922 A | 8/1978 | Alers et al. | |
| 4,197,751 A * | 4/1980 | Vilkomerson et al. | 73/633 |
| 4,258,576 A * | 3/1981 | Vilkomerson et al. | 73/633 |
| 4,462,255 A * | 7/1984 | Guess et al. | 73/633 |
| 4,637,256 A * | 1/1987 | Sugiyama et al. | 73/633 |
| 4,646,754 A | 3/1987 | Seale | |
| 4,757,818 A * | 7/1988 | Angelsen | 600/446 |
| 4,785,816 A | 11/1988 | Dow et al. | |
| 4,787,247 A | 11/1988 | Wuchinich et al. | |

(Continued)

*Primary Examiner* — J M Saint Surin
(74) *Attorney, Agent, or Firm* — Gottlieb, Rackman & Reisman, P.C.

(57) ABSTRACT

A mechanical scanning device is composed of an oscillating beam onto which a transducer is mounted, part of which is flexible such that the beam will oscillate at a frequency between 8 and 15 Hz when mechanically energized. To sustain oscillations, energy is supplied by means of two electromagnetic coils acting on two permanent magnets mounted on either side of the beam. In order to improve the linear performance of the probe, feedback control was employed. A position sensor along with supporting electronics was designed to provide control signal for the feedback system.

6 Claims, 28 Drawing Sheets

(56) References Cited

U.S. PATENT DOCUMENTS

| | | |
|---|---|---|
| 5,179,276 A | 1/1993 | Hakamata |
| 5,329,194 A | 7/1994 | Dow et al. |
| 5,351,692 A | 10/1994 | Dow et al. |
| 5,402,789 A | 4/1995 | Dow et al. |
| 6,198,956 B1 | 3/2001 | Dunne |
| 6,231,186 B1 | 5/2001 | Broadus et al. |
| 6,246,898 B1 | 6/2001 | Vesely et al. |
| 6,294,775 B1 | 9/2001 | Seibel et al. |
| 6,767,696 B2 | 7/2004 | Howard et al. |
| 6,837,855 B1 | 1/2005 | Puech |
| 6,887,203 B2 | 5/2005 | Phillips et al. |
| 7,051,582 B2 | 5/2006 | Akiyama |
| 7,093,490 B2 | 8/2006 | Kono et al. |
| 7,532,375 B2 | 5/2009 | Rosman et al. |
| 2005/0043629 A1 | 2/2005 | Rabiner et al. |
| 2005/0101869 A1 | 5/2005 | Burba et al. |
| 2007/0242330 A1 | 10/2007 | Rosman et al. |

\* cited by examiner

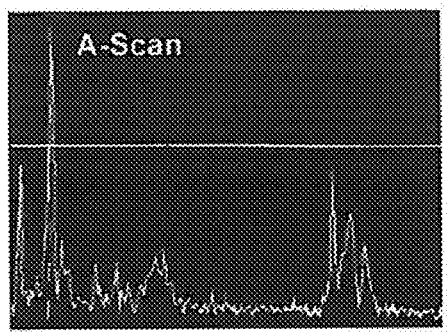
FIG. 1.1
(PRIOR ART)
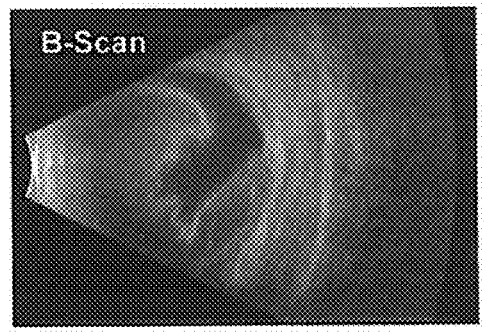
FIG. 1.2
(PRIOR ART)
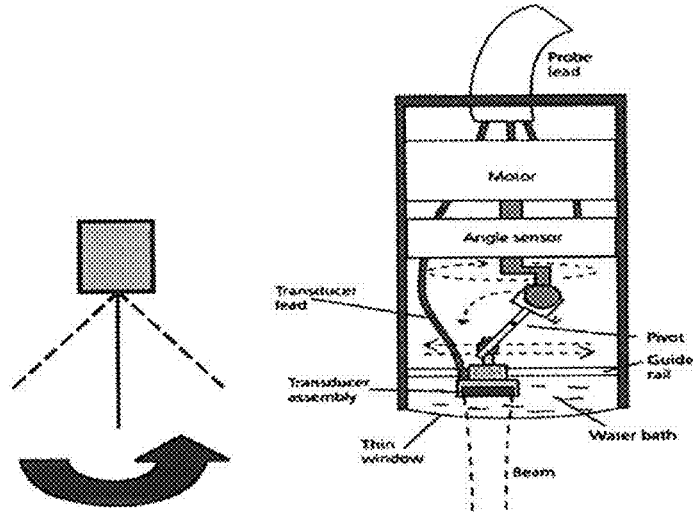
FIG. 1.3
(PRIOR ART)
FIG. 1.4
(PRIOR ART)

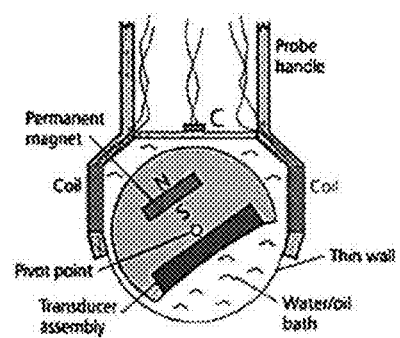
FIG. 1.5
(PRIOR ART)

- The controller was implemented in software using Matlab/Simulink environment.
- Quanser Q8-USB data acquisition board provides as D/A and A/D.
- LT1210 current feedback amplifier provides bidirectional current driving capability.
- HMC1501 magnetic displacement sensor senses beam position.
- LT1167 amplifies the position signal.

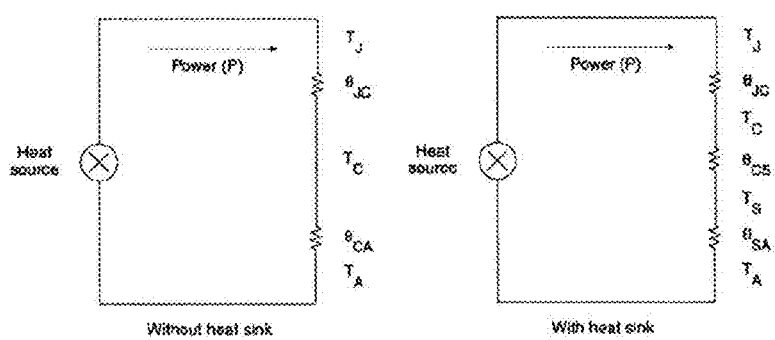
*Figures 15A, 15 B: Thermal Circuit for with and without heat sink*

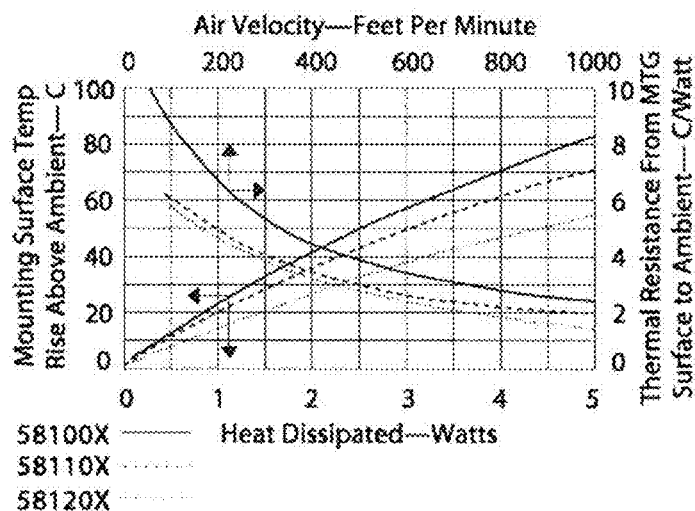
Fig. 16 Thermal Curve for the heat sink
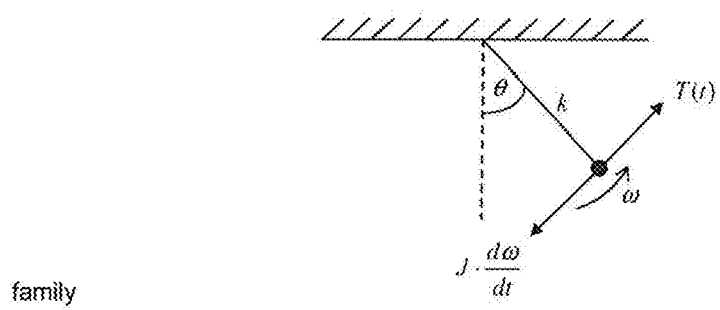
family
Fig. 17 Rotational mass on a spring model

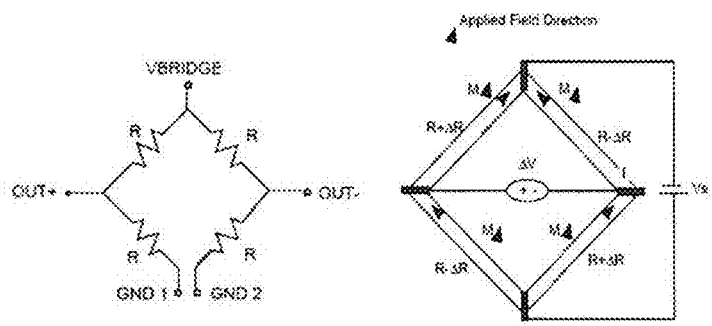
Fig. 18A: HMC-1501 Internal Structure    Fig. 18B
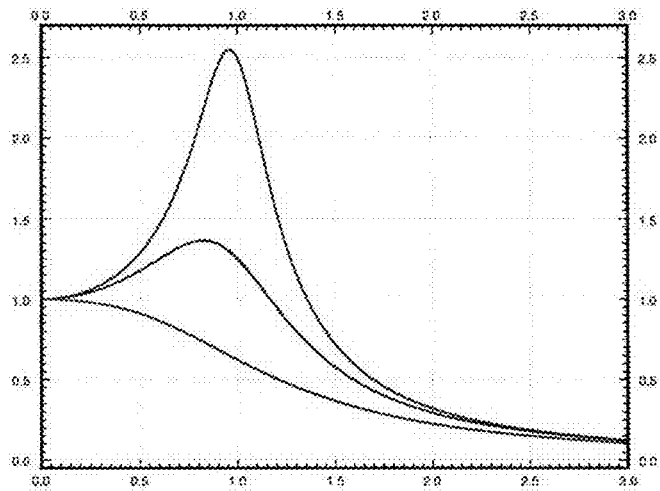
Figure 18C Resonance characteristics with different damping constants

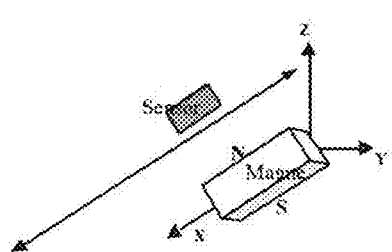
Fig. 19 Sensor orientation
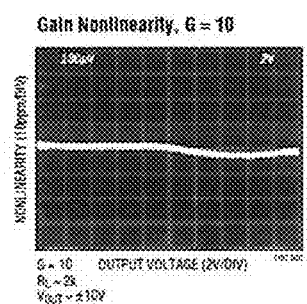 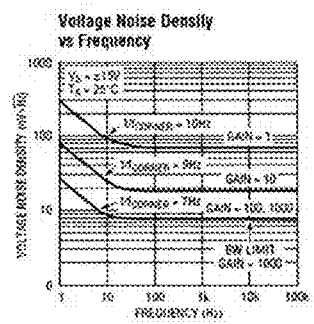
FIG. 20A              FIG. 20B

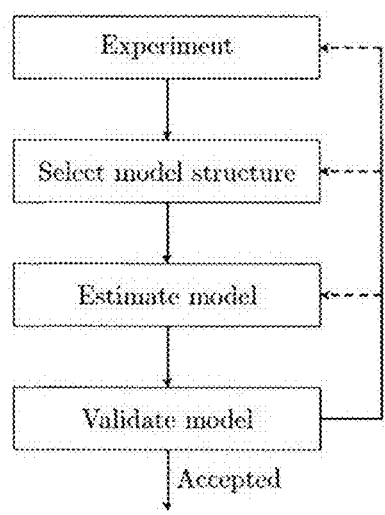
Figure 21: System Identification Procedure
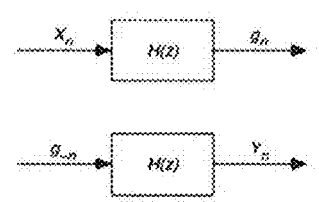
Figure 22: Forward Backward Filtering Algorithm

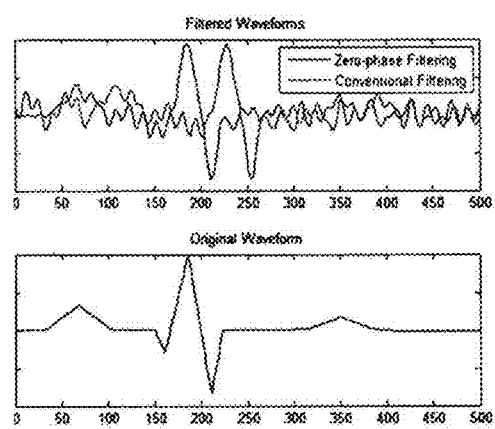
Fig. 23 A, 23B zero Phase filtering
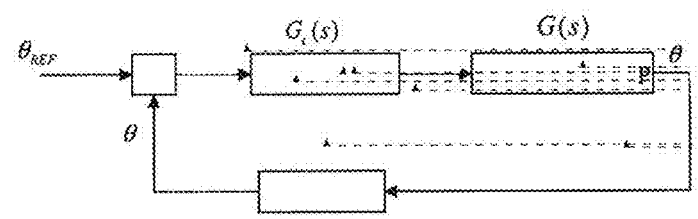
Figure: 24 Feedback control circuit

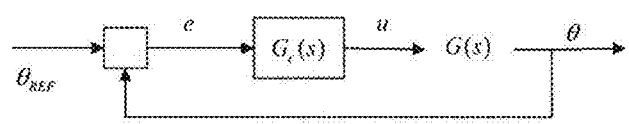
Fig. 25 *Closed loop system block diagram with appropriate transfer functions*
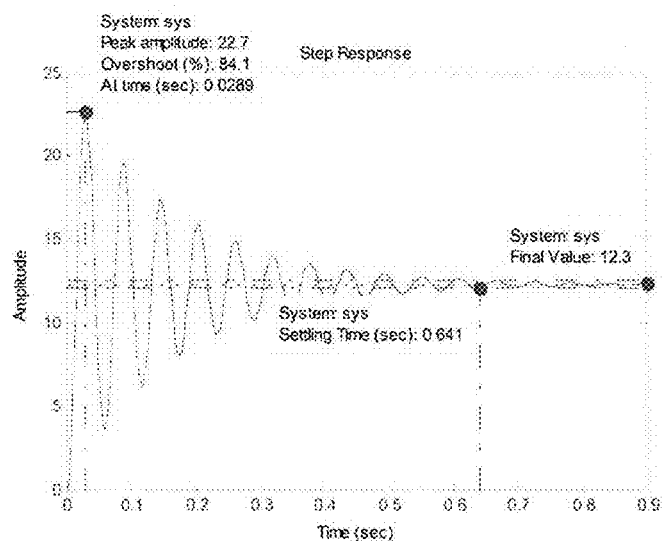
Figure 26A: *Step Response of the open loop system with the identified parameters*

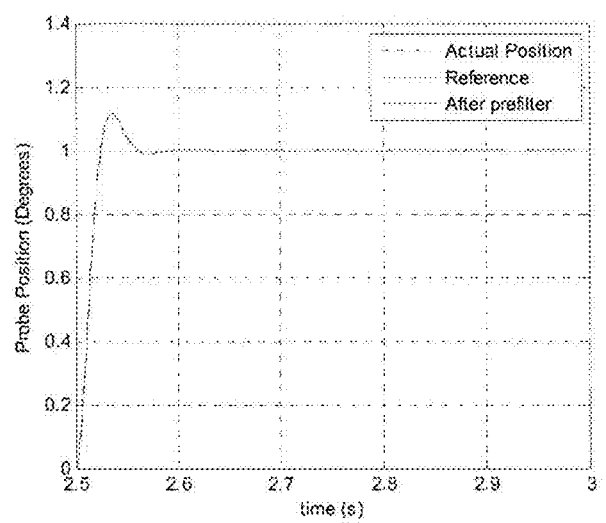
Figure 26B: Step Response of the closed loop system with the controller as well as the pre-filter

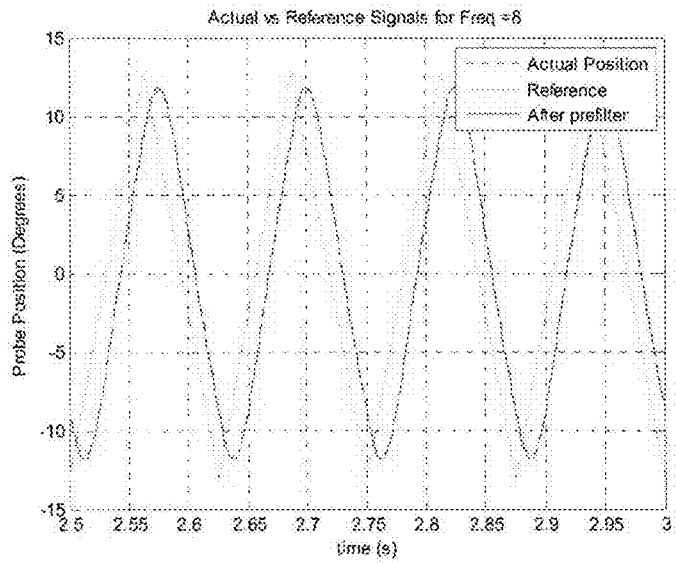
Figure 26C: Reference Signal vs output position signal
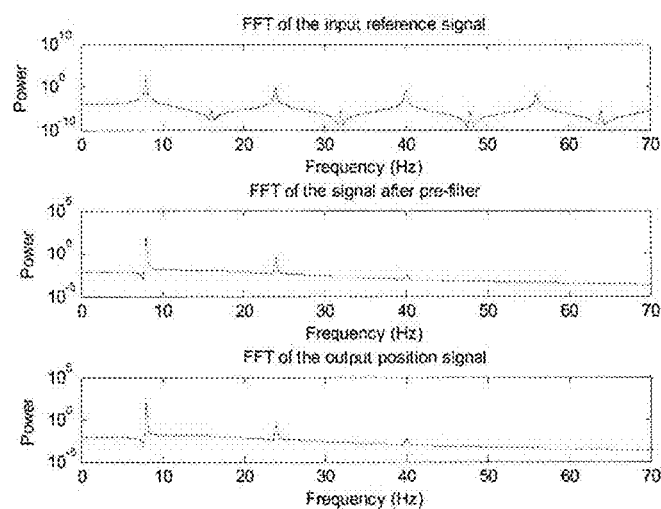
Figure 26D: Frequency Spectrum Comparison of the signals

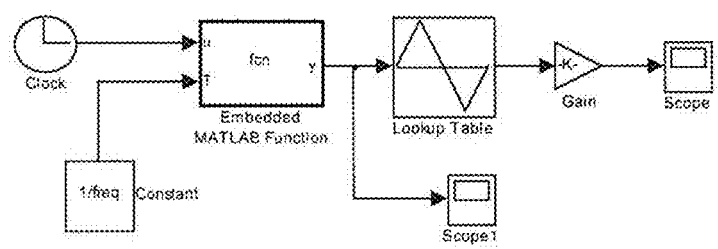
Figure:27B Simulink model for creating the reference signal

System Implementation in Software

System Implementation in Hardware

```
PSPICE CODE FOR CURRENT DRIVER CIRCUIT SIMULATIONS

*Current Driver
Vsig Vsig 0 DC 0 AC 1 SIN(0V 0.5V 15)
vccp vccp 0 5V
vccn vccn 0 -5V
.include S:\ECEDrive\Yu_Excel\Simulations\Models\lt1210.sub
        *$
           .model D1N4148  D(Is=2.682n N=1.836 Rs=.5664 Ikf=44.17m
Xti=3 Eg=1.11 Cjo=4p
        +           M=.3333 Vj=.5 Fc=.5 Isr=1.565n Nr=2 Bv=100 Ibv=100u
Tt=11.54n)
        *$ RL neg temp 7.18 *Resistance of the coil
RG 0 neg 2
L1 temp out 1MH
D1 out temp1 D1N4148
RF1 temp1 neg 10K
D2 temp2 out D1N4148
RF2 temp2 neg 10K
*.let ac gaindB=dB(v(out)/v(vsig)) gphase=180*ph(v(out)/v(vsig))/3.14
Xtest vsig neg vccp vccn out comp LT1210
*.DC Vsig -5 5 0.1
*.AC DEC  5  0 50
.TRAN 1mS 0.3S
.probe
.end
```

Fig. 27E

ULTRASONIC SCANNING PROBE WITH A TUNING FORK-TYPE OSCILLATOR AND FEEDBACK CONTROL THEREOF

RELATED APPLICATIONS

This application is a continuation-in-part of application U.S. application Ser. No. 12/643,186, filed Dec. 21, 2009, claiming priority to U.S. Provisional Application. Ser. No. 61/149,057 filed Feb. 2, 2009; and claims priority to U.S. Provisional Patent Application Ser. No. 61/474,009 filed Apr. 11, 2011; 61/513,731 filed Aug. 1, 2011 and Ser. No. 61/569,466 filed Dec. 12, 2011; all incorporated herein by reference in their entirety.

BACKGROUND OF THE INVENTION

A. Field of Invention

This application pertains to an ultrasonic scanning probe having a tuning fork-type oscillator supporting an ultrasonic generator, as well as a control circuit for controlling the lateral movement of the oscillator.

B. Description of the Prior Art

Ophthalmic ultrasound is a diagnostic medical imaging technology that utilizes high frequency sound waves to create cross-section B-scan images and time-amplitude A-scan images of the globe and orbit of the eye. As the sound waves strike intraocular structures, they are reflected back to the probe and converted into an electric signal (FIG. 1.1). Ultrasound is a safe, noninvasive diagnostic tool that provides instant feedback for the evaluation of various ophthalmic disorders. Ophthalmic ultrasound instruments use pulse-echo system, which consists of a series of emitted pulses of sound, each followed by a brief pause (microseconds) for the receiving of echoes and processing to the display screen. A short acoustic pulse is generated mechanically by a piezoelectric crystal, which acts as a transducer to convert electric energy into ultrasound. At every acoustic interface, some of the echoes are reflected back to the transducer, indicating a change in tissue density. The echoes returned to the probe are converted back into an electrical signal and processed as ultrasound images. Currently, ophthalmic ultrasound machines use frequencies in the range of 8 to 80 MHz, compared with 2 to 6 MHz typically used in other fields of diagnostic ultrasound.

A-scan, B-scan and ultrasound biomicroscopy are the most commonly used ultrasound instrumentation techniques. A-scan is a one-dimensional display of echo strength over time. The vertical spikes correspond to echo intensity and are shown the horizontal axis as function of time (FIG. 1.1). It uses frequency of 10 to 12 MHz and is mainly used for axial eye length measurements. A-scan sonography is particularly useful in ophthalmology as a biometric tool where the axial measurement of the globe (the region in the eye from anterior cornea to retinal surface) is a prime data element in the calculations for determining the appropriate power of an intraocular lens implant for cataract surgery.

B-scan is a two dimensional display of echoes using horizontal and vertical orientations to show shape and location (FIG. 1.2). It is an important tool for the clinical assessment of various ocular and orbital diseases. In situations in which normal examination is not possible, such as lid problems, corneal opacities dense cataracts, or vitreous opacities, diagnostic B-scan ultrasound can accurately image intraocular structures and give valuable information on the status of the lens, retina, and other parts. Ultrasound biomicroscopy is an ultrasound instrument that uses frequencies from 35 to 80 MHz for the acoustic evaluation of anterior segment of the eye. Interpretation of the images for all the above ultrasound techniques is based on knowledge of both the normal and abnormal ocular anatomy, and an understanding of the physical principles of ultrasound.

In a pulse-echo-imaging system, one can either scan the transducer in a freehand form and detect the position of the transducer, or control the motion of the transducer. The former was once a popular technique; however the latter is the current technology. A single transducer is scanned mechanically at intervals across the eye that is elliptically shaped. At each controlled mechanical stopping point, sound is sent across and echoes are received. The bright dots in each trace on the display indicate the front and back wall echoes of the eye. By scanning across the eye, multiple lines produce the image of the eye on the display. In order to maintain fidelity of the 2-dimensional images of the near and far structures in the eye, the ultrasonic beams have to diverge from virtually the same point. This means that the image has to be generated by a single beam originating from the same point, being deflected in different angles to build a sector image. This is usually achieved by a single transducer or array sending a single beam that is stepwise rotated, either mechanically or electronically. The subsequent lines of the image are then formed by a slight angular rotation, making the beam sweep across a sector as shown in FIG. 1.3.

Mechanical scanning is currently the industry standard in ophthalmic applications like A-Scan and B-scan as it is mostly useful in the 15 to 20 MHz range. Despite the disadvantages associated with moving parts of the scanner like wear and tear, vibration, and so on, the amounts of acoustic noise these scanners produce, compared to phased-array probes, are much smaller. Two types of mechanical scanning systems are commonly used. In a linear mechanical scanner, the transducer is driven back and forth inside an enclosed water bath rather than air at the end of a handheld probe (FIG. 1.4) as the transducer-air interface, acting to acutely refract the sound wave, would result in total internal reflection of the sound wave, and therefore no transmission of the sound would take place. The cable between the probe and the machine contains a coaxial cable, carrying signals to and from the transducer, and leads carrying the drive current to the electric motor and the signal from the position sensor.

Another type of mechanical scanning probe is the sector scanner. The probe contains similar features to the linear scanner but it is designed to produce a rocking motion. The probe is made compact by having the necessary drive components built into and closely around the rocking transducer assembly as shown in FIG. 1.5.

In most non-ophthalmic instruments, linear and phased array transducers have replaced mechanically scanned transducers described above. These arrays can electronically steer and focus the ultrasound beam at various depths and can provide higher refresh rates. However, the cost and technical complications with building arrays increases with frequency. Hence, the current industry trend is to either select expensive arrays to maintain the quality of ultrasonic images or to select the simpler mechanical scanner and compromise the quality, especially for higher frequencies. There is no optimum solution that incorporates both the relative technical simplicity and low building cost of a mechanical scanner and the high performance capability of phased arrays in one device.

SUMMARY OF THE INVENTION

The main objective of the project is to develop an efficient, cost effective and high performing mechanical sector scanning probe for use in ophthalmic diagnostic ultrasonic instruments. The probe is to be equipped with feedback control mechanism that can adapt to varying conditions and provide better performance than the standard open loop scanner. Although control theory is a vastly mature and well studied field which has been in use in many modern engineering designs, its application in ophthalmic probes is new. This work is mainly intended to be used in B-scan ultrasonography in which an oscillating sound beam is emitted by a transducer, passing through the eye and imaging a slice of tissue; the echoes of which are represented as a multitude of dots that together form an image on the screen shown in FIG. 1.1. Feedback control is used to better regulate the motion of the oscillating probe, which greatly improves the rate at which one can send the ultrasonic beams. This would greatly enhance one's capability to record clearer images, that are free from common artifacts associated with open loop probes, and would provide a more superior diagnostic instrument than what is commonly used today.

BRIEF DESCRIPTION OF THE FIGURES

FIGS. 1.1 and 1.2 show typical A and B scans;
FIGS. 1.3-1.5 show various existing ultrasonic scanners;
FIGS. 15A and 15B show a thermal circuit of the invention with and without a heat sink;
FIG. 16 show typical characteristics of some standard heat sinks;
FIG. 17 shows a mass rotating on a spring;
FIGS. 18A and 18B show the circuit diagram and a current flow diagram for the sensor used in the invention;
FIG. 18 C shows the Resonance characteristics with different damping constants
FIG. 19 shows a sensor orientation with respect to the magnet in the present invention;
FIGS. 20A and 20B show the characteristics of an instrumentation amplifier used for the prototype;
FIG. 21 shows a flow chart for validating a model of the invention;
FIG. 22 shows a schematic for the forward and backward filtering algorithm;
FIGS. 23A and 23B show filtered wave forms and an original unfiltered waveform;

FIG. 24 shows a block diagram of the feedback control circuit;
FIG. 25 shows a block diagram of the closed loop system with some characteristic transfer functions;
FIGS. 26A and 26*b* show the open loop and closed loop response of the control circuit;
FIG. 26C shows a comparison of the reference and the output signals;
FIG. 26D shows a the various signals in the system in the frequency domain;
FIGS. 27A-D show the experimental setup for simulating the invention; and
FIG. 27E shows a program listing used in the simulation.

DETAILED DESCRIPTION OF THE INVENTION

Chapter 1—General Discussions

Figure 2:
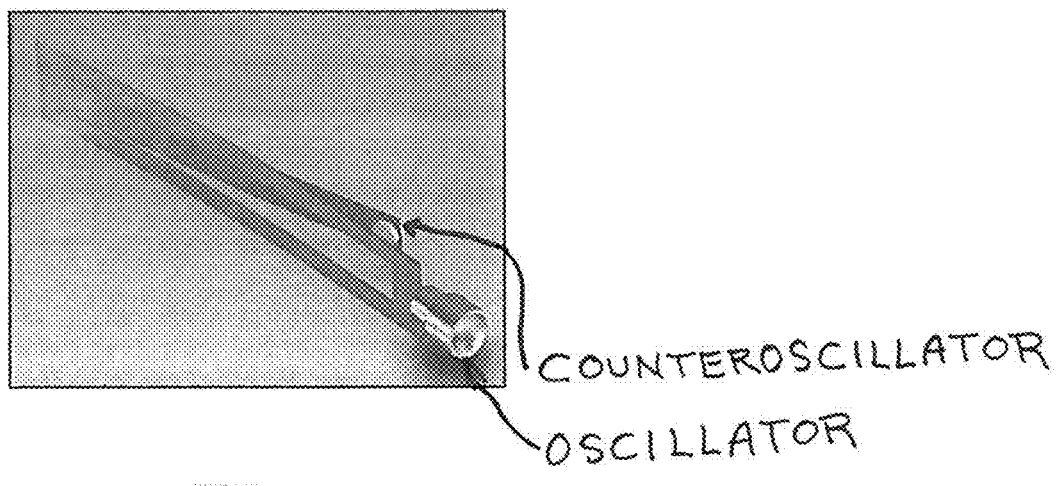
FIG. 2 shows a diagrammatic orthographic view of a tuning fork with an ultrasonic generator constricted in accordance with this invention.

The present invention based on the tuning form model described in above-identified application Ser. No. 12/643,186, filed Dec. 21, 2009 in which an ultrasonic transducer is mounted on a beam that is flexible and oscillates at about 15 Hz when mechanically energized. In order to get acceptable efficiency for the oscillator, and for ergonomic reasons, a counter-oscillator is proposed to counteract all vibration from main oscillator. The counter-oscillator is a second beam, energized separately, and phased locked 180° to the main oscillator. The illustration of this model is shown in FIG. 2.

Figure 3:
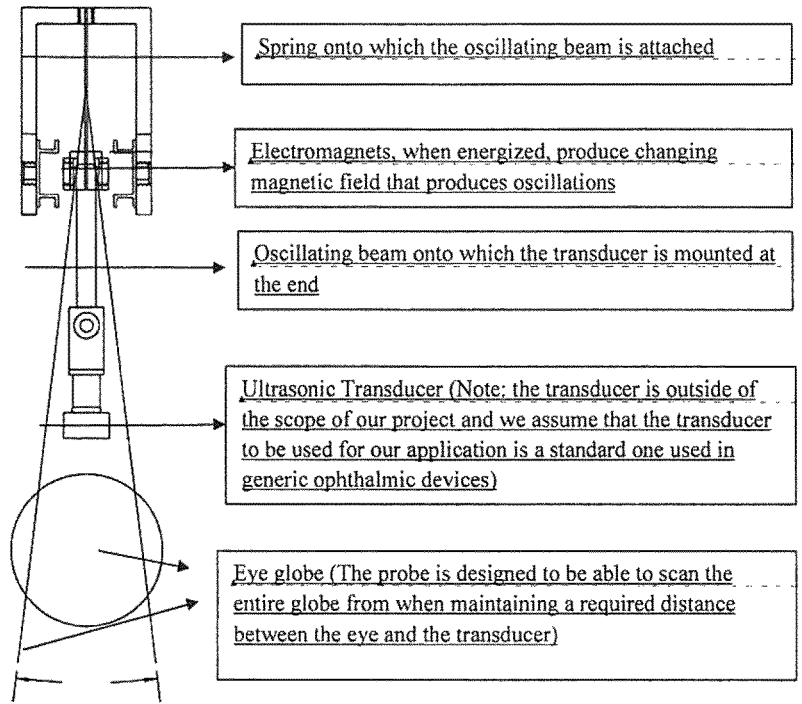
FIG. 3 shows a front view of a prototype constructed in accordance with this invention.

Based on the model proposed, the designed system comprises of a beam with two permanent magnets on either side of the beam. Current passes through the coils to create the magnetic field that interacts with two magnets mounted on the beam to simultaneously push and pull the beam back and forth and hence produce oscillations. FIG. 3 illustrates the major components of the probe design. The major difference between the model proposed and the prototype implementation in this thesis is that the current prototype does not include a counter-oscillator. Also, the operating frequency range for the prototype model is from 8 Hz to 15 Hz. This system is also different from the proposed model in that extra set of springs which are attached to the oscillating beam and these springs are the only flexible part of the probe. This implies that the beam itself, onto which the ultrasonic transducer is mounted, is rigid.

Based on the normal medical practice requirements, the desired angle for the oscillations is set at ±8° to be able to scan the entire eye. This angle ensures that the entire globe of interest can be scanned from within a safe distance. Also, the image above is in scale with a real life prototype, all of which would be in a housing size characteristic of the industry standard handheld device.

Figure 5:
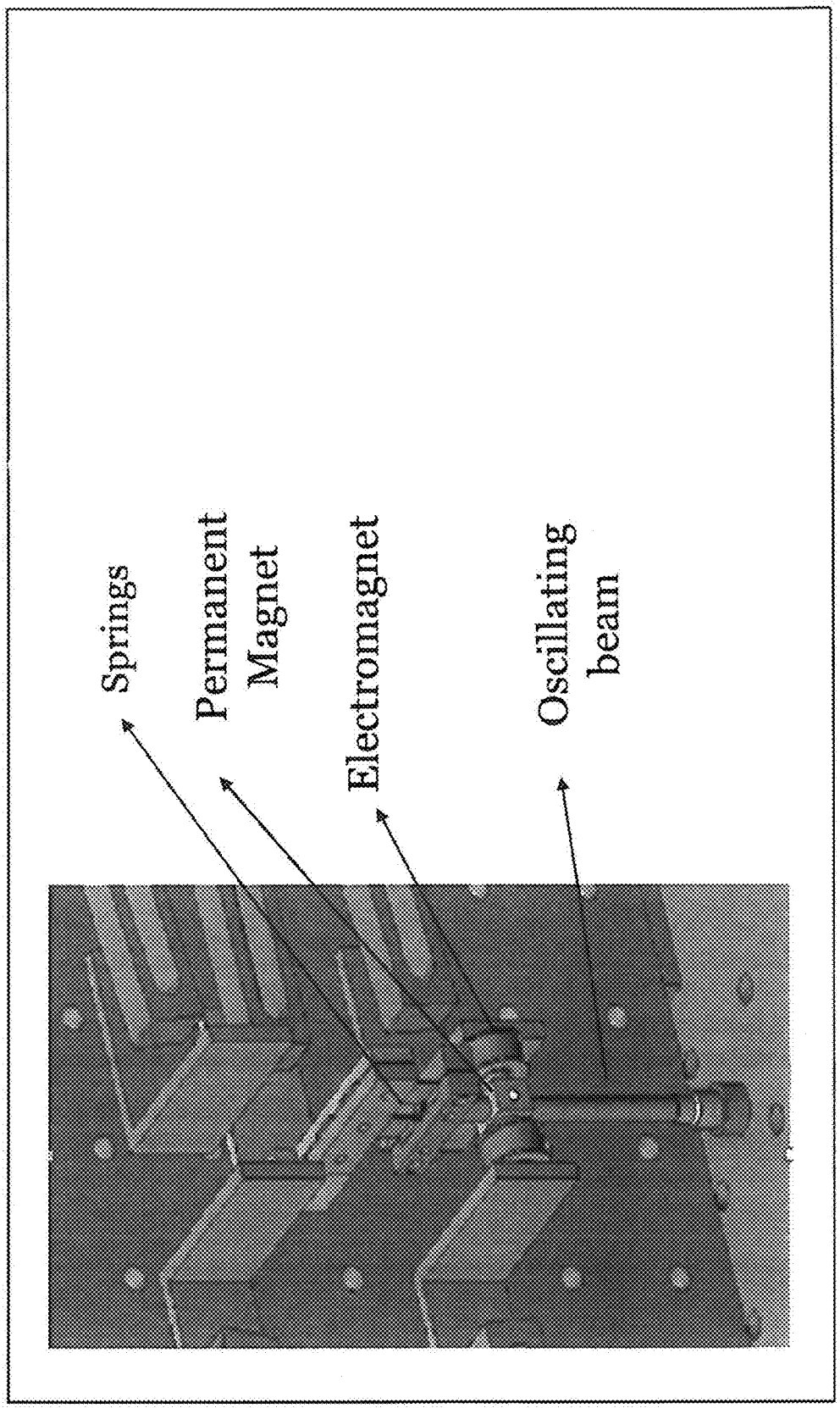
FIG. 5 shows a diagrammatic top view of the device of FIG. 3 used to scan an eye of a patient.

To be competitive in the open market, the sizes of the probe would have to be similar to those available in the market. Hence, the dimensions of the probe were governed by this constraint. This also restricted other probe parameters such as the size of the coils and the length of the springs. The system design was accomplished by breaking the system down into individual components like the current driver circuit, the sensor circuit and so on as represented in FIG. 5.

The current driver circuit was designed and implemented to drive the beam to sufficient angles at required frequencies. An appropriate sensor circuit was also designed and implemented to accurately detect the position of the beam. The controller itself was designed and implemented in software and interacted with the external prototype via A/D and D/A.

Figure 6:
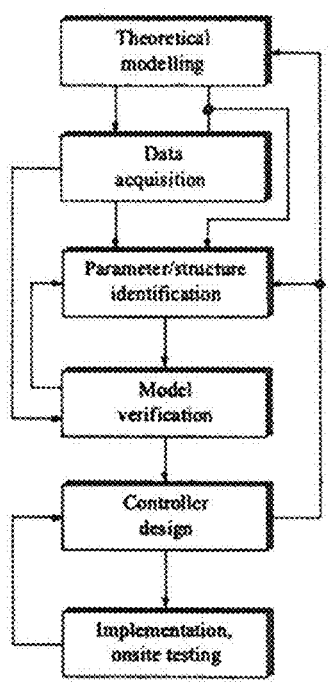
FIG. 6 shows a flow chart of the process used to design the present invention.

The design procedure illustrated in FIG. 6 was followed to accomplish the feedback control system and this required identifying and validating mathematical model of the constructed probe prototype. The probe model developed characterizes the current-angle relationship of the oscillator, describing the motion of the beam as a function of current going into the coils. The parameters of the model were identified from least squares fit using experimental data. Extensive testing of the identified model was performed in software for all frequencies to meet the required angle requirements and oscillation behavior. One of the main challenges in designing such a system was the tradeoff that had to be made between the performance of the beam and the current being drawn into the coils.

As shown in FIG. 6, control design is inherently an iterative process and in designing the desired system, one has to conduct several iterations of modeling and parameter estimation. By having a basic understanding of the physics behind the motion of the probe beam, a linear second order differential equation for the motion behavior was predicted. A grey box modeling technique was then used to estimate the associated parameters in the model and hence implement and test the system based on the estimated values.

This work consists of four parts. First, based on the specification, a complete mechanical scanning probe prototype with feedback control was developed. The detailed explanations of all the individual components and implantation considerations are provided in chapter 2. Second, a mathematical model for the oscillation mechanism of the probe was developed and best fit algorithm was used to estimate the parameters of the model; this is described in chapter 3. Third, based on the parameters obtained from chapter 3, a suitable controller was designed and implemented to track the reference signal as closely as possible; this is described in chapter 4. Last, the full system was implemented and the performance tested and parameters tuned to meet the specifications; this is described in chapter 5.

Chapter 2: System Components: Detailed Description

The complete system comprised of various components as shown in FIG. 5. The controller was implemented in software using Matlab/Simulink environment. A data acquisition card from Quanser was used as the digital to analog converter (D/A) and analog to digital converter (A/D) interface. LT1210, a high slew rate current feedback amplifier was used in the current driver configuration in the power board as a bidirectional voltage to current converter. HMC1501, a magnetic displacement sensor was used as the position sensor, the signal of which is amplified by LT1167 instrumentation amplifier to be fed in to the software via the A/D.

The main objective of incorporating feedback control, which is what distinguishes this design from existing devices, is the possibility of being able to acquire high quality position signal. This position signal then could be used to accurately ping the ultrasonic transducer at precise points and get crisp images that are free from jitters and other artifacts. This would not only ensure higher frame rate capability when displaying the obtained images into a screen, but also present the probe as the best of its class in competitive market.

Figure 7:
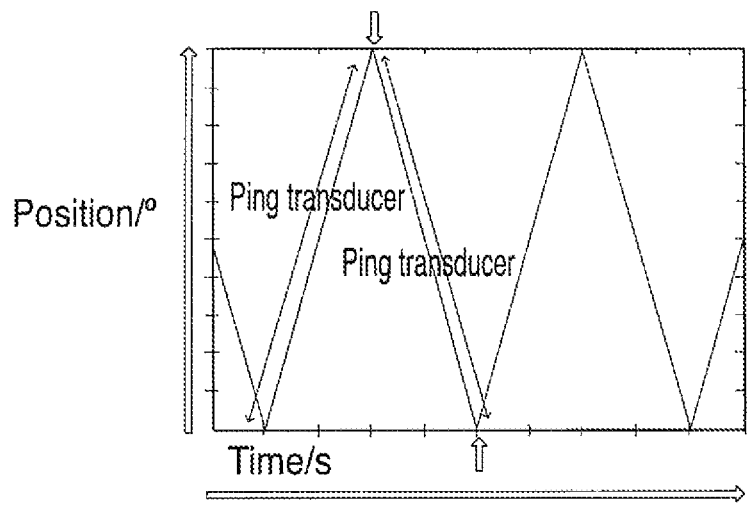
FIG. 7: shows a graph of an Ideal Probe Motion Profile.

The aim is to be able to set a linear motion behavior for the beam. This allows one to scan the eye in both directions more linearly, which would significantly reduce the artifacts when overlapping the time scan signals to form the B-Scan images. This ideal behavior that week seek in terms of performance is presented in FIG. 7.

The need for the behavior above arises from the fact that a sinusoidal signal becomes nonlinear with increasing angle and since the specifications require the probe angle amplitude at ±8°, it is necessary to introduce feedback control to keep linearity in the motion of the beam. In the following sections, all the different components (shown in blocks in FIG. 5) required to implement the system and to be able to meet the performance goals are explained in detail.

2.1 Power Board

Figure 8:
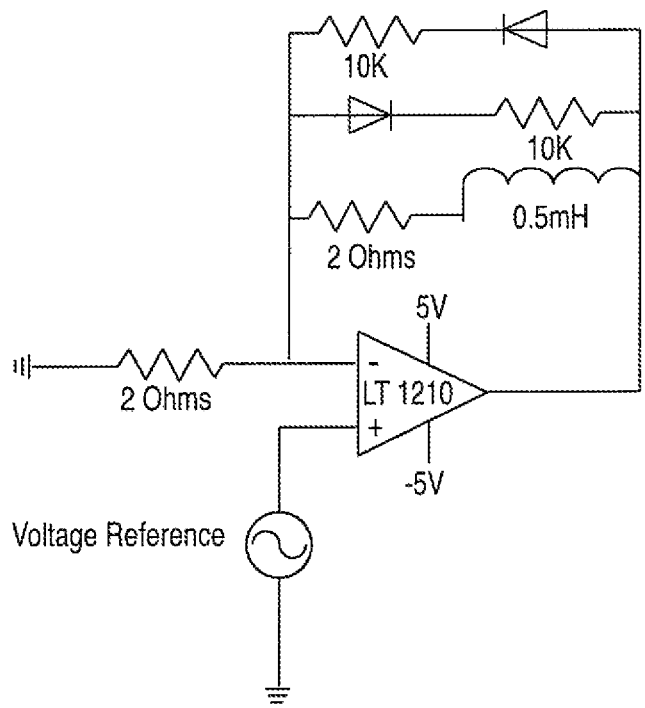
FIG. 8 shows a Schematic of the current drive circuit.

The goal of the circuit in the power board as shown in FIG. 8 is to receive a voltage command from the controller through a D/A converter and produce oscillating current through the coils so as to produce oscillations in the beam. LT1210, a high current capable current feedback amplifier is used in a voltage to current converter configuration to inject current into the coils, represented as 0.5 mH inductor. Two diodes in series with 10K resistors are used as sinks for the voltage spikes generated by the sudden change of current in the coils. A current feedback amplifier was chosen instead of the normal voltage current feedback amplifier because of its unique capability to sink and source high currents which would provide us a lot of flexibility while designing the system. Since, the oscillations of the probe are made possible by the induced magnetic field, it is important to understand the significance of the current driver circuit.

Figure 9:
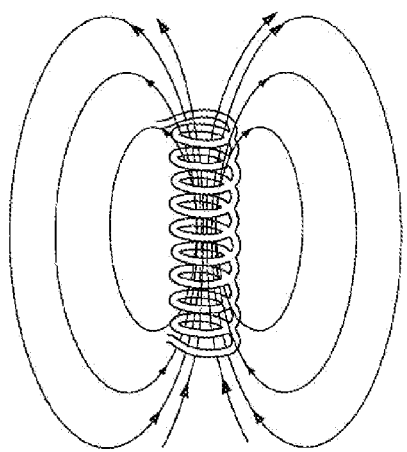
FIG. 9 shows Magnetic Field lines around a current carrying coil

When a current is passed through a circular coil, a magnetic field is produced around it. The lines of force are circular near the wire, but they become straight and parallel towards the middle point of the coil as illustrated in FIG. 9.

The magnitude of magnetic field produced by a current carrying wire at its center is directly proportional to the current passing through the circular wire, and inversely proportional to the radius of the circular wire. A current carrying coil hence behaves as a thin disc magnet, whose one face is a north pole and the other face is a south pole. The strength of magnetic field produced by a current carrying circular coil can be increased by increasing the number of turns of wire in the coil, by increasing the current flowing through the coil and by decreasing the radius of the coil. The magnetic field near the centre of the coil is $B=\mu_0$ in where n is the number of turns per unit length of the solenoid and $\mu_0=4\pi*10E-7$ Tm/A.

Since the magnetic field is proportional to the product ni, the number of turns in the windings per length n and the current i can be chosen to minimize heat losses, as long as their product is constant. Since the power dissipation, $P=i^2R$, increases with the square of the current, the power lost in the windings can be minimized by reducing i and increasing the number of turns n proportionally. This is precisely the reason why most electromagnets have windings with many turns of wire. Also, the coil is a large inductor and resists changes in the current through its windings due to which sudden changes in the coil current cause large voltage spikes across the coil. In order to mitigate this problem, the double diode configuration was adopted to prevent voltage spikes by providing a path for the current to circulate through the winding until the energy is dissipated as heat. The diode is connected across the winding such that it is reverse-biased during steady state operation and doesn't conduct. When the supply voltage is removed, the voltage spike forward-biases the diode and the reactive current continue to flow through the winding, through the diode and back into the winding.

LT1210 is a current feedback amplifier with high output current capability and is mostly directed towards driving high currents through capacitive loads. The current feedback amplifiers are transimpedance operational amplifiers which are mostly popular due to their high speed and high slew rate. They are mostly used in broadcast video systems, radar systems, IF and RF stages, RGB distribution systems and many other high speed circuits. In the designed system, it is used as a high power bidirectional current source to drive the load (electromagnets). The open loop differences between the current feedback amplifiers and the regular voltage feedback amplifiers are illustrated in FIGS. 10A, 10B.

Figure 10A:
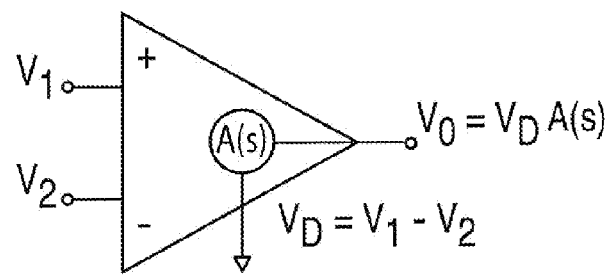
FIGS. 10A and 10B show an Ideal Current Feedback Amplifier vs Ideal Voltage Feedback Amplifier Open Loop Characteristics.
Figure 10B:
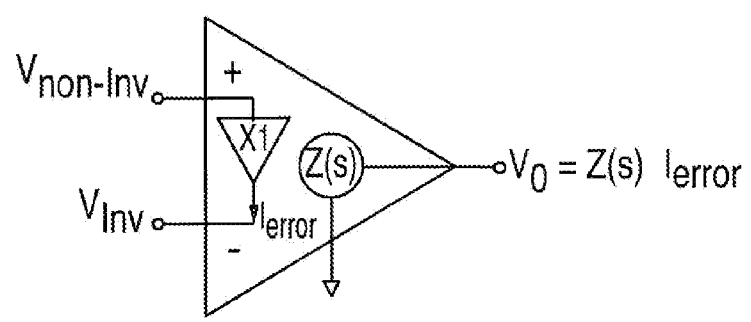
Figure 11A:
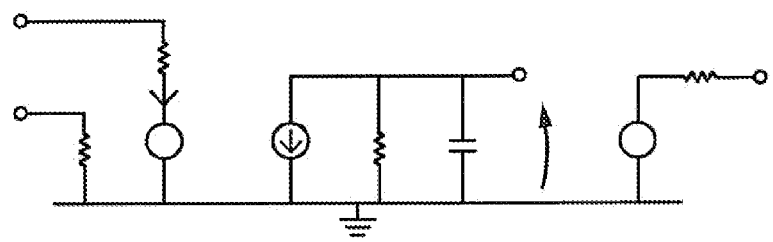
FIGS. 11A and 11B show Small signal model of Current Feedback Amplifier vs Ideal Voltage Feedback Amplifier.
Figure 11B:
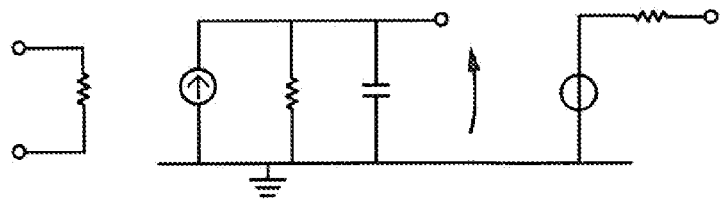

Notably, from FIGS. 10A. 10B, one can observe that there is a unity gain buffer between the two inputs of the current feedback amplifier. Ideally, this buffer has infinite input impedance and zero output impedance. Therefore, the ideal open loop terminal characteristics of this amplifier include infinite non-inverting input impedance, zero inverting input impedance and zero output impedance. Based on the small-signal model of the current feedback amplifier (FIGS. 11A, 11B), one can observe that $R_t$ is the equivalent resistance at the gain node. The output resistance of the input voltage buffer, $1/g_{mi}$ is the input resistance at inverting node, and the input resistance of the input buffer, $r_{b1}$ is the input resistance of the noninverting node. The output resistance of the output voltage buffer $1/g_{m0}$, is the output resistance.

Current Feedback Amplifiers are used in high frequency amplification because they have current-controlled gain and a current-dominant input. Being a current device, the current feedback amplifier does not have the Miller-effect problem that the voltage feedback amplifier has. The input structure of the current feedback amplifier sacrifices precision for bandwidth, but it can achieve usable bandwidths ten times the usable voltage feedback amplifier bandwidth. The input impedances of current feedback amplifier vastly differ from that of a voltage feedback amplifier because of the difference in respective circuit configurations. In the voltage feedback amplifier, both input impedances match and the input signal looks into an emitter-follower circuit that has high input impedance. The current feedback amplifier, however, has a radically different input structure that causes it to have mismatched input impedances. The non-inverting input lead of the current feedback amplifier is the input of a buffer that has very high input impedance while the inverting input lead is the output of a buffer that has very low impedance.

Figure 12A:
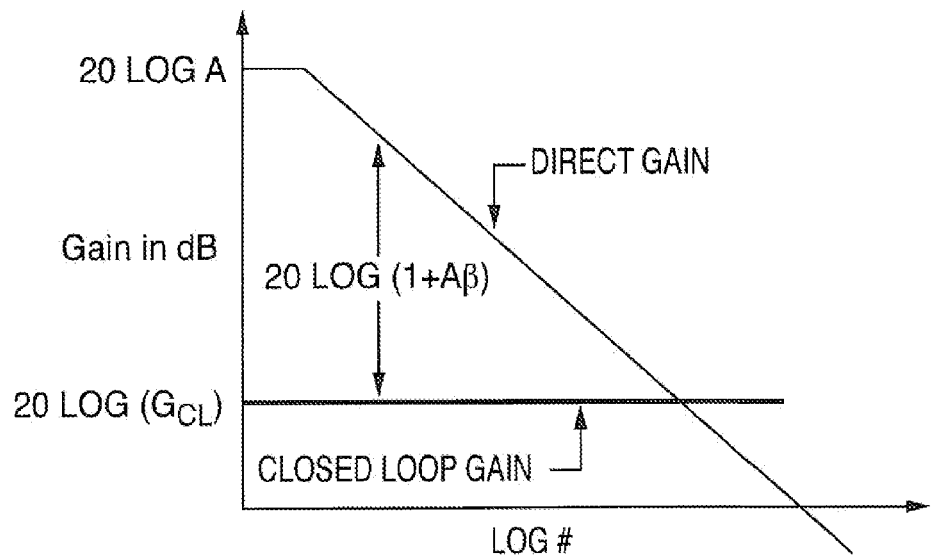
FIGS. 12A and 12B show Frequency Response of Current Feedback Amplifier vs Voltage Feedback Amplifier.
Figure 12B:
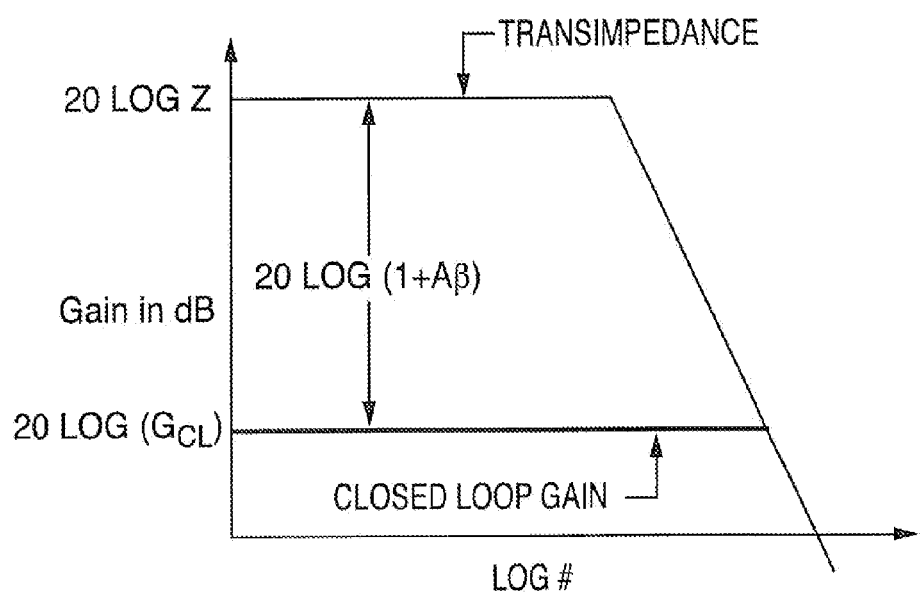

As far as the noise performance is concerned, similar noise voltage and noise currents at the non-inverting input characterize the two circuits. The output noise in current feedback amplifier is dominated by the noise current and it provides a higher gain-bandwidth product at the expense of losing open-loop gain. The Miller effect causes the direct gain to fall off at high frequencies as shown in FIGS. 12A. 12B, thus error increases as frequency increases because the effective loop gain decreases. The absence of the Miller effect enables the current feedback amplifier's frequency response to hold up far better.

The most important consideration of current feedback amplifiers in regards to the design is that the impedance at the inverting input sets the bandwidth and therefore the stability of the amplifier. It should be resistive, not capacitive as stray capacitance from any node to ground adversely affects the performance of the current feedback amplifier. Even small capacitances (as small as couple of pFs) from any node to ground could cause 3 dB or more of peaking in the frequency response. Stray capacitance across the current feedback amplifier's feedback resistor, quite unlike that across the voltage feedback amplifier's feedback resistor, could cause instability.

2.1.1 Current Driver Circuit Performance Testing

Figure 13A:
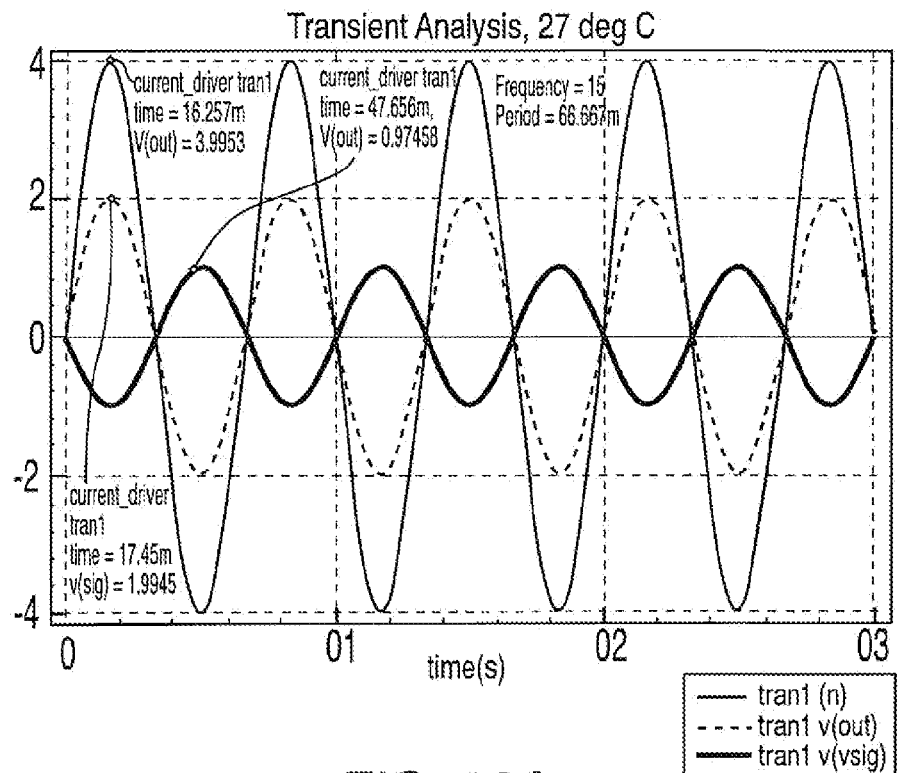
FIGS. 13A-13D show various test results on the circuit.
Figure 13B:
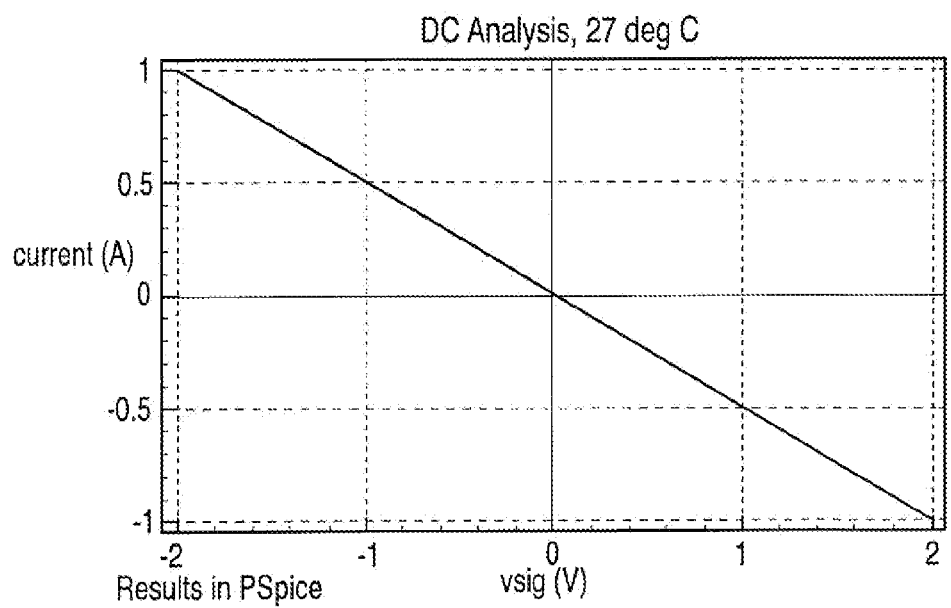

The current driver circuit was tested in simulation (PSpice) and in hardware to verify its performance. While testing in simulation, the main objective was to observe if the amplifier was saturating. With an internal current limit set at 1 A to avoid significant power consumption in the coils, the simulation showed the successful implementation of the circuit configuration to supply 1A current in either direction which was accomplished by running DC analysis in PSpice as shown in FIG. 13B. Also, in order to test the performance of the amplifier at the highest frequency requirement of 15 Hz, transient analysis was performed and the results were favorable as shown in FIGS. 13A, 13B.

Figure 13C:
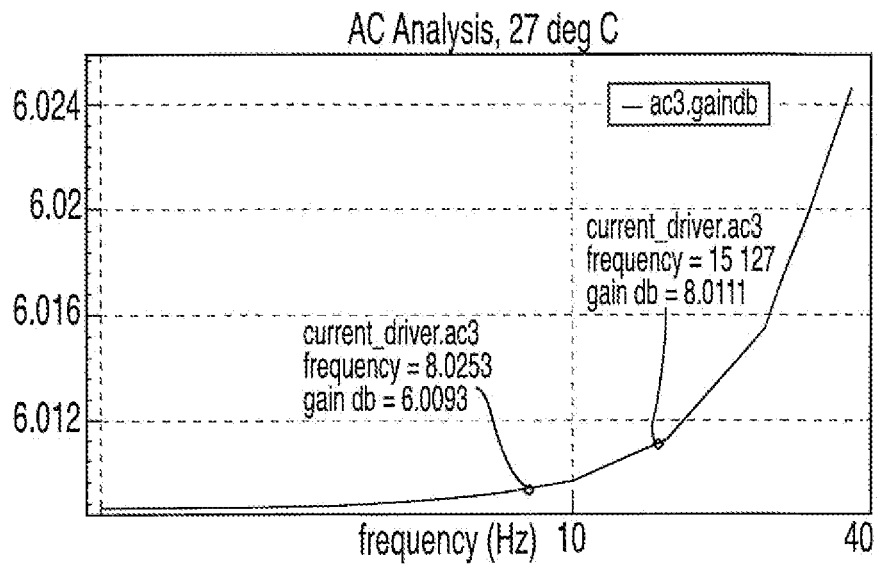
Figure 13D:
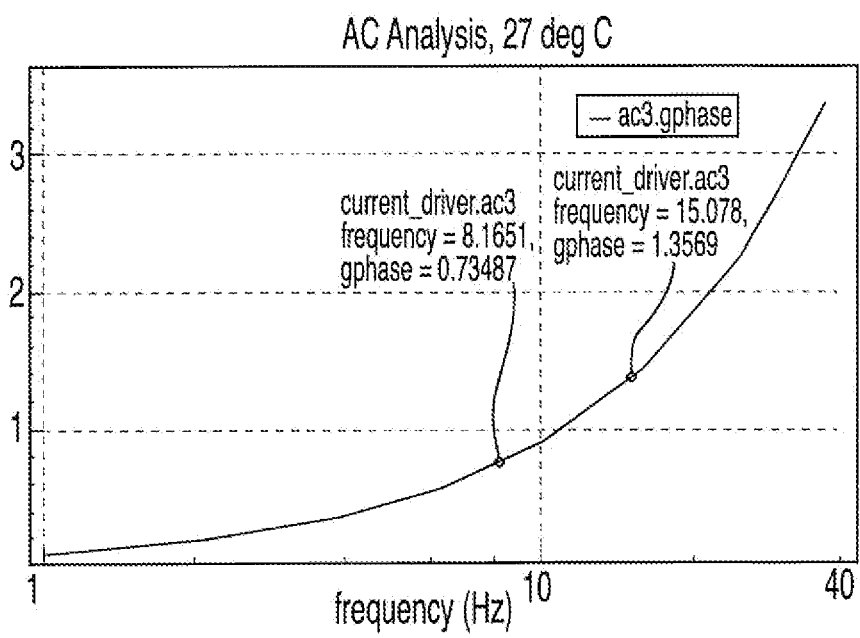

Also, AC analysis was used to verify the absence of any significant amount of distortion in terms of gain as well as phase for the required frequency range of 8 to 15 Hz. This analysis (as shown in FIG. 13C, 13D) proved that the circuit provided stable performance for all frequencies.

Figure 14A:
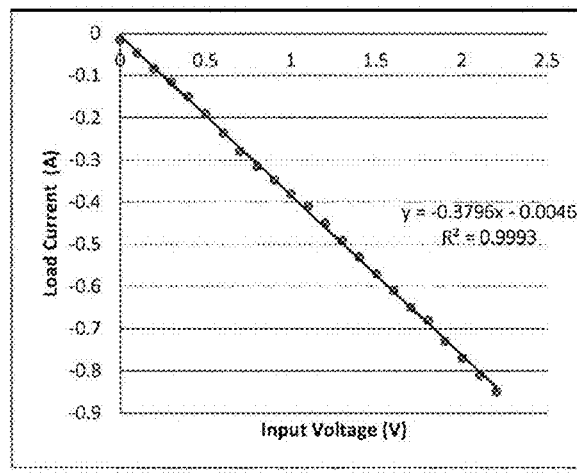
FIGS. 14A and 14B show the input and output characteristics of the current driver.
Figure 14B:
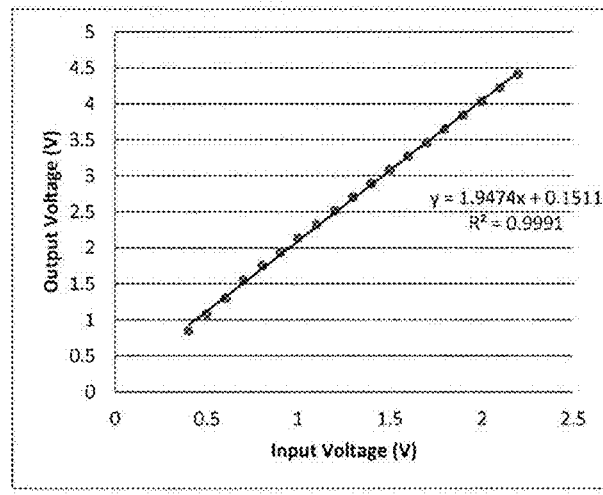

The circuit configuration for the current driver circuit was also tested in hardware to verify linear operation as well as saturation conditions as shown in FIGS. 14A. 14B. The data presented in FIGS. 14A, 14B correspond to an input source of ±10 VDC.

2.1.2 Thermal Analysis

Thermal management is an important design consideration for the setup, mainly because of the high current flowing through the circuit that dissipates significant amount of heat. This heat must be dissipated to maintain operating temperatures within specifications, especially for the current feedback amplifier. Some operating conditions (high current situations) lead to more power dissipation and will require external thermal solutions, including heat sinks. The thermal energy transfer efficiency of heat sinks is due to the low thermal resistance between the heat sink and the ambient air. Thermal resistance is the measure of a substance's ability to dissipate heat, or the efficiency of heat transfer across the boundary between different media. A heat sink with a large surface area and good air circulation (airflow) gives the best heat dissipation.

A heat sink helps keep a device at a junction temperature below its specified recommended operating temperature. With a heat sink, heat from a device flows from the die junction to the case, then from the case to the heat sink, and lastly from the heat sink to ambient air. Since the goal is to reduce overall thermal resistance, one can determine whether a device requires a heat sink for thermal management by calculating thermal resistance using thermal circuit models and equations. These thermal circuit models are similar to resistor circuits using Ohm's law. FIGS. 15A and 15B shows a thermal circuit model for a device with and without a heat sink, reflecting the thermal transfer path via the top of the package.

TABLE I

Thermal Circuit Parameters

| Parameter | Name | Units | Description |
|---|---|---|---|
| $\theta_{JA}$ | Junction-to-ambient thermal resistance | °C./W | Specified in the data sheet |
| $\theta_{JC}$ | Junction-to-case thermal resistance | °C./W | Specified in the data sheet |
| $\theta_{CS}$ | Case-to-heat sink thermal resistance | °C./W | Adhesive compound thermal resistance specified by manufacturer |
| $\theta_{CA}$ | Case-to-ambient thermal resistance | °C./W | Solved for by equation |
| $\theta_{SA}$ | Heat sink-to-ambient thermal resistance | °C./W | Solved for by equation and specified by the heat sink manufacturer |
| $T_J$ | Junction temperature | °C. | The maximum junction temperature as specified for the device |
| $T_A$ | Ambient temperature | °C. | Usually the maximum ambient air temperature specified for the device on the device's data sheet |
| $T_S$ | Heat sink temperature | °C. | The heat sink's maximum measured temperature near the device |

TABLE I-continued

Thermal Circuit Parameters

| Parameter | Name | Units | Description |
|---|---|---|---|
| Tc | Device case temperature | °C. | The device package's maximum measured temperature |
| P | Power | W | Total rate of heat dissipation from the device while operating. Use the maximum value for selecting a heat sink |

To determine the necessity of a heat sink, the junction temperature is calculated using the following equations: Without a heat sink, $$\theta_{JATotal} = \theta_{JC} + \theta_{CA} = \frac{T_J - T_A}{P} \quad (2.1)$$

And with a heat sink, $$\theta_{JATotal} = \theta_{JC} + \theta_{CS} + \theta_{SA} = \frac{T_J - T_A}{P} \quad (2.2)$$

If the calculated junction temperature ($T_J$) is more than the specified maximum allowable junction temperature ($T_{JMAX}$), an external thermal solution (heat sink, added air flow, or both) is required. When using a ±5V supply, the following thermal analysis is performed.

$P_D$=10V·0.24 A−((0.24 A)²·7Ω)=1.9968 W $T_A$=40° C.

$$\theta_{JA} = 35 \frac{°C}{W}$$

$T_{jMAX}$=150° C.

$T_j$=1.9968·35+40=109.88° C. (<150° C.)

Using a ±10V supply, the following analysis is performed.

$P_D$=20V·0.8 A−((0.8 A)²·7Ω)=11.52 W $T_A$=40° C.

$$\theta_{JA} = 35 \frac{°C}{W}$$

$T_{jMAX}$=150° C.

$T_j$=11.52·35+40=443.2° C. (>150° C.)

Based on the analysis above, it can be observed that, when the system is powered with ±10V supply, heat sink (along with air flow) is indeed in order to meet the operating specifications of the device. As a sample heat sink, 58100 flat back extruded heat sink from Aavid Thermalloy is used as a reference. Some of the notable specifications for this particular heat sink are as follows:

Outline: 16.25 mm×16.25 mm, Height: 1.000" (25.40 mm), Material: Aluminum, Power Dissipation @Temperature Rise: 2.5 W @50° C., Thermal Resistance @Forced Air Flow: 4° C./W @500 LFM.

Forced ventilation or forced airflow can reduce a heat sink's thermal resistance. In cases where the thermal resistance to free convection is known and the temperature gradient remains constant, it is possible to calculate the thermal resistance of a heat sink of a given length when subjected to forced ventilation at various air flow speeds. The characteristics of the selected heat sink with forced airflow are shown in FIG. 15. Using the values from the thermal curves in FIG. 14 analysis for the ±10V supply is conducted as follows.

$P_D$=20V·0.8 A−((0.8 A)²·7Ω)=11.52 W $T_A$=40° C.

$$\theta_{JA} = 4 \frac{°C}{W}$$

$T_{jMAX}$=150° C.

$T_j$=11.52·4+40=86.08° C. (<150° C.)

Hence, it can be observed that in order to fully meet the thermal specifications of the device, a heat sink with forced air cooling is required. The above equations above thus help determine the requirement of appropriate heat sinks for the various components in the design. The primary ways to improve the thermal characteristics is to increase airflow, lower the power consumed or even reduce the maximum ambient temperature. Whenever the ambient conditions cannot be modified enough to remove the need for a heat sink, one needs to carry out the thermal analysis to find the heat sink required.

2 Probe Design Considerations

The most challenging aspect of the system design process was the design of the actual probe itself. At the initial stages of the design process, a one coil configuration was suggested, mainly because of the spacing and clearances inside the probe housing this configuration offered. However, it was soon discovered that even when high current was driven through the coil, the magnetic force produced was not enough to sustain the beam to the required angles. Hence, a two-coil configuration was proposed that immediately addressed this issue as it almost doubled the angle performance. This configuration also made more ergonomic sense from a product development point of view. The size of the beam itself as well as the springs was set by considering the actual size of the probe, which had to be handheld sizes.

One of the most challenging aspects of developing this system with a product development aspect in mind was that everything had to make economic sense. All the parts of the system would either have to be off the shelf parts or they should be able to be machined at a low cost for mass volume. After the dimensions of the beam were set, the weight became a major issue. Two options were proposed: a plastic molded beam that would be much lighter and would require less force to produce oscillations and a brass (metal) beam that might be heavier but would be more sturdy and durable during the proof of concept phase. It was eventually decided to keep the probe design in brass. It also meant that during the prototyping stage, a brass probe was cheaper and easier to construct than a plastic one. The constructed prototype with its major components is shown in FIG. 16.

Yet another challenge in being able to construct a open loop system that meet the angle requirements was the choice of suitable material for the spring. The set of springs that with which the prototyping was started provided decent performance but it was soon realized that much better performance could be achieved by decreasing the thickness of the springs. After some iterations of changing the spring thickness, an optimum thickness was selected in which the spring would provide good oscillations and yet be durable. Experiments were carried out with different materials but none of them performed as well as the springs that were used in the design initially.

2.3 Resonance Considerations

When the frequency of the periodic external force applied (through the coils) to the oscillating beam is related in a simple way to the natural frequency of the system, resonance may occur which builds up the oscillations to large magnitudes that the entire oscillating mechanism may fall apart. Although resonance finds useful applications in acoustics, radio reception, NMR spectroscopy and so on, because of the destructive capabilities of resonance, it is to be avoided as much as possible, especially because the designed system is a vibrating one Hence, to be able to avoid resonance, it is necessary to have a quantitative understanding of how and when it occurs. Usually resonance presents itself in two ways. The amplitude resonance is the one where amplitudes rise to tremendous levels and phase resonance is the one that introduces angular shift between the external drive and the oscillating object. For the mass-spring consideration, only amplitude resonance will be analyzed.

Based on the prior knowledge of physical systems and observations of the model, the system model can be simplified to a typical angular mass on a spring system, where the moment of inertia is equivalent to the mass on a linear motion. Let moment of inertia J>0 be connected by a spring with spring constant k>0 to a fixed wall. There is an external Torque T(t) acting on the rotational mass. Finally, there is some friction measured by c≥0 as the mass slides along the air. Let θ be the angular displacement of the mass (θ=0° is the rest position), with θ growing to the right (away from the vertical equilibrium) as shown in FIG. 17.

The force exerted by the spring is proportional to the compression of the spring by Hooke's law. Therefore, it is kθ in the opposite direction. Similarly the amount of force exerted by friction is proportional to the angular velocity of the mass. By Newton's second law $$J \cdot \frac{d^2\theta}{dt^2} = T(t) - c \cdot \frac{d\theta}{dt} - k \cdot \theta \qquad 2.3$$

$$J \cdot \frac{d^2\theta}{dt^2} + c \cdot \frac{d\theta}{dt} + k \cdot \theta = T(t) \qquad 2.4$$

This is a linear second order ordinary differential equation. Since a driving torque is being provided, the motion of the beam is forced. The setup is: J is moment of inertia, c is friction coefficient, k is the spring constant and T(t) is the external force acting on the mass. Using the concept of Fourier series a generic periodic forcing function is assumed as $$T(t) = T_0 \cdot \cos(\omega t) \qquad 2.5$$

Let $p = \frac{c}{2 \cdot J}$ and $\omega_0 = \sqrt{\frac{k}{J}}$ in Equation 2.4, $$\theta'' + 2 \cdot p \cdot \theta' + \omega_0^2 \cdot \theta = \left(\frac{F_0}{J}\right) \cdot \cos(\omega t) \qquad 2.6$$

Solving the differential equation, the following transient response characteristic is obtained $$x_c = \begin{cases} C_1 e^{r_1 t} + C_2 e^{r_2 t} \mid c^2 > 4kJ \\ C_1 e^{-pt} + C_2 t e^{-pt} \mid c^2 = 4kJ \\ e^{-pt}(C_1 \cos(\omega_1 t) + C_2 \sin(\omega_1 t)) \mid c^2 < 4kJ \end{cases} \qquad 2.7$$

where, $\omega_1 = \sqrt{\omega_0 - p^2}$

Solving for the particular solution, $x_p = A\cos(\omega t) + B\sin(\omega t)$ $$A = \frac{(\omega_0^2 - \omega^2)T_0}{m(2\omega p)^2 + m(\omega_0^2 - \omega^2)^2}, \qquad 2.8$$

$$B = \frac{2\omega p T_0}{m(2\omega p)^2 + m(\omega_0^2 - \omega^2)^2}$$

$$C = \sqrt{A^2 + B^2} \qquad 2.9$$

$$C = \frac{T_0}{J\sqrt{(2\omega p)^2 + J(\omega_0^2 - \omega^2)^2}} \qquad 2.10$$

$$x_p = \qquad 2.11$$

$$\frac{(\omega_0^2 - \omega^2)T_0}{J(2\omega p)^2 + J(\omega_0^2 - \omega^2)^2}\cos(\omega t) + \frac{2\omega p T_0}{J(2\omega p)^2 + J(\omega_0^2 - \omega^2)^2}\sin(\omega t)$$

$$\text{If } \omega = \omega_0, A = 0, B = C = \frac{T_0}{2J\omega p}. \qquad 2.12$$

$x_c$ is the transient solution and $x_p$ is the steady periodic solution. The general solution to the equation describing the system is $x = x_c + x_p = x_{tr} + x_{sp}$ where $x_{tr}$ is the transient response and $x_{sp}$ is the steady periodic response.

One needs to address the phenomenon of resonance differently in the system, in which damping in the air and the spring is present. This is accomplished by analyzing maximum value of the amplitude of the steady periodic solution. Let C be the amplitude of $x_{sp}$. C is plotted as a function of ω (with all other parameters fixed), to find its maximum and this ω is called the resonance frequency. The maximal amplitude C(ω) is the resonance amplitude. A sample plot for three different values of damping constant is given in FIG. 18C. Resonance amplitude grows as damping gets smaller, and any resonance effects disappear when damping is large.

To find the maximum one needs to find the partial derivative of C(ω) with respect to ω.

$$\frac{d[C(\omega)]}{d\omega} = \frac{-4\omega(2p^2 + \omega_0^2 - \omega^2)T_0}{J((2\omega p)^2 + J(\omega_0^2 - \omega^2)^2)^{\frac{3}{2}}} \qquad 2.13$$

This is zero either when ω=0 or when $2p^2 + \omega^2 - \omega_0^2 = 0$. In other words, C'(ω)=0 when $\omega = \sqrt{\omega_0 - 2p^2}$ or ω=0. Hence, $\sqrt{\omega_0 - 2p^2}$ is the resonant frequency for the system. This analysis presents a specification for selecting system parameters like the tightness of the spring, the overall mass of the vibrating beam and so on.

2.3 Position Sensor

HMC-1501 Magnetic Displacement Sensor was chosen as the position sensor mainly because of its noncontact nature, cheap price, sufficient resolution, small packaging and low power requirements. HMC-1501 is an Anisotropic Magneto-Resistive (AMR) sensor that is used to sense the location of moving objects. By attaching to a magnet to the oscillating beam, the relative direction of the resulting magnetic field is used to determine the position electronically. Magnetoresistive sensors bring a unique feature by measuring the angle direction of a field from a magnet versus the strength of a magnetic field. A permanent magnet provides the magnetic field, which has the function of keeping the sensor in saturation mode, minimizing effects of stray magnetic field and providing a linear operating range for selected sensor pairs.

The HMC 1501 (see FIG. 18A) comprises of a saturated mode Wheatstone bridge to measure magnetic field direction. The resistance of all four bridge legs is the same. The saturation mode is when external magnetic fields are above certain field strength level (called saturation field). When in saturation mode, the magnetic moments in the device are aligned in the same direction of the field. Therefore, the output of the device only reflects the direction of the external magnetic field and not the strength. The saturation field of this type of sensors is around 50 Gauss. Magnetic fields in this magnitude can be easily provided by any low cost permanent magnet.

The bridge elements change their resistance when a magnetic field is applied across the silicon die with the thin films of magneto-resistive ferrous material forming the resistive elements. The magneto-resistance is a function of $\cos 2\theta$ where $\theta$ is the angle between the applied magnetic field and the current flow direction in the thin film. When the applied magnetic field becomes 50 Gauss or larger, the magnetization of the thin films align in the same direction as the applied field; and becomes the saturated.

In this mode (see FIG. 18B), $\theta$ is the angle between the direction of the applied field and the bridge current flow, and the magnetoresistive sensor is only sensitive to the direction of the applied field and not the amplitude. The bridge power supply causes current to flow through the bridge elements. The magnet is a crucial part in the system, because it converts the motion to be measured to the sensors and is attached to the object moving, that is the probe. It is best for the magnet to be mounted with the north and south poles perpendicular to the sensor as demonstrated below.

There are few requirements when selecting the magnet. The magnet should provide a magnetic field strong enough to saturate the magnet field around the sensor. The magnetic field could be in different directions, but the total field strength in the device plane (X-Y plane) should be higher than 50 gauss when using the HMC-1501. A simple dipole magnet usually has the strongest field near its poles, and field decreases with the distance. If the magnet strength is not sufficient to saturate the sensor array, it will have errors. In the worst case, if stray fields dominate some sensor locations, the system could have random position indication or a systematic error depending on the type of stray field. For example: An AlNiCO cylinder magnet with 0.25" diameter has a field strength 700 gauss at its surface. With a 0.25" gap between the sensor array and magnet, the field at the sensors is about 170 gauss. This is enough field strength to maintain the sensor in the saturation condition. However, if the gap increases to 0.5", the field strength not enough to saturate the complete region around the sensor. A NdFeB magnet with the same dimension provides 3000 Gauss field at its surface and is able to satisfy the saturation condition at an air gap of 0.5".

Temperature coefficient of the magnet is not critical in this design approach, because the sensor output does not rely on magnetic field strength. However, in order to have accurate measurements, the magnet should be assured to provide magnetic field large enough to maintain saturation of the sensors in the whole operating temperature range. The drift in the material constant affects both the bridge sensitivity and offset. This should be accounted with temperature monitoring circuitry.

As an implantation analysis, at 120 mV p-p and instrumentation amplifier gain of 25, the output voltage swing is about 3Vp-p centered about 2.5V (1V to 4V). With a bridge offset specification ±7 mV/V and 5V supply, the bridge yields ±35 mV. After the gain, the offset is ±850 mV which is within A/D power rails. Some of the notable Specifications of the HMC-1501 which are relevant to the system are as follows.

Supply Current: 1 mA
Bandwidth: 5 MHz
Output p-p @Vb=5V, @field=80 Oe: 120 mV
Bridge Offset @Vb=5V, $\theta$=0°: 3 mV/V (typ)
Resolution @10 Hz, Vb=5V: 0.07°
Power Consumption @Vb=5V: 5 mW
Noise @1 Hz, Vb=5V: 100 nV/sqrt(Hz)
Case Dimension (exclusive of pins): 5 mm×4 mm×1.3 mm.

2.4 Instrumentation Amplifier

LT1167 is a low power, precision instrumentation amplifier that uses one external resistor to set gains. The low voltage noise of 7.5 nV/sqrt(Hz) is not compromised by low power dissipation. The part's high accuracy (10 ppm maximum nonlinearity, 0.08% max gain error coupled with the simplicity of being able to set the gain using just a single resistor makes it ideal to amplify the position signal in the system.

The amplifier (see FIG. 20A, 20B) was tested with the actual signal and it met the performance requirement in terms of noise and distortion. Because of the low gain (~20) applied to the position signal, the nonlinearity never became an issue. The single-ended output voltage referenced to the voltage on the REF pin for the amplifier is $$V_{OUT}=V_{REF}+\text{Gain}*(V_{IN}^+ - V_{IN}^-) \qquad 2.14$$

where, Gain=(49.4 K$\Omega$/$R_G$)+1

Solving for gain set resistor gives, $$R_G=49.4 \text{ K}\Omega/(G-1) \qquad 2.15$$

The single instrumentation amplifier is easier to work with when integrating in the system due to the few number of discrete parts involved in comparison to a custom built regular three op amp instrumentation amplifier. This makes the design process less complicated which is the reason for its usage.

Chapter 3: System Identification

System Identification is the art and science of building mathematical models of dynamic systems from observed input-output data. It is closely related to control theory, mainly because the identified system models are directly used for control design. Before designing a controller, one needs to have a good understanding of the equations describing the model. A general procedure for system is to take measurements of the behavior of the system and the inputs to determine a mathematical relation between them without realizing the details inside the system itself. Commonly, two types of models are used in system identification: grey box model and black box model. In the grey box model, the model obtained from the basic physical principles is not sufficient because of the missing values of some of the parameters. For example, the spring is subject to the friction but the amount of friction is unknown. Hence, it is necessary to collect experimental data and proceed to a tuning of the unknown parameters until the outputs predicted by the model match the observed data. In the black box model the internal structure of the system is unknown and there are no physical principles to rely on. The only way to identify the system is to collect data and use them to infer the relationship between input and output. For the designed system, grey box modeling, which is also known as parameter identification, was used since the form of the system is known (typical second order mass-spring system).

System identification plays a crucial role in making the design work as it is typically the first step. However, is it also one of the most complicated ones because of its close connection to physical reality (unlike analysis and design that are usually performed on a mathematical model). The algorithm presented on in FIG. 21 was used to accomplish system identification.

The identification of the process model involves collecting experimental data and using that data to estimate the parameters in the selected model. This step is repeated until a certain criterion is met, which is usually based in terms of the smallest expected square error between observed outputs and predictions. One cannot stress enough on the importance of iterating through the steps to meet the criterion goals. It is almost always necessary to go back in the procedure to determine a number of different models, to try out various model structures, and at times, even repeat the whole experiment.

3.1 System Identification Methodology

Based on the specifications for the system, the operating frequency was 8 Hz to 15 Hz. Hence, the system performance for the entire frequency range had to be characterized. Initially, only was set of parameters were identified to correspond to the entire frequency range of intended use of the probe. The methodology used was as follows.

A continuous sinusoidal signal consisting of frequencies from 8 Hz to 15 Hz with an increment of 1 Hz was created and used as the reference signal.

Using sampling frequency of 1 KHz, the data for probe behavior was collected for 10 s for each individual frequency, hence obtaining 10,000 samples for each frequency.

The collected data were then fit to the assumed model and based on the error criterion, the model parameters (along with the model structure) were either rejected or accepted.

However, the error criterion term, defined as the error index, using this approach was very high. This meant that when the collected data points did not fit into the specified model structure. In order to correct this issue, a range of cutoff frequencies for the filters were used. However, this did not improve the error index much.

As a result, a slightly different procedure was used.

A continuous sinusoidal signal consisting of frequencies from 8 Hz to 15 Hz was created and used as the reference signal.

Using a sampling frequency of 1 KHz, the data for probe behavior was collected from 10 s for each individual frequency, hence obtaining 10,000 samples for each frequency.

Only the data collected between 5 s and 10 s (or 5000 sample points in total) for each frequency were selected for parameter estimation. These data were selected because the probe was operated under steady state.

In order to fit the data to the model structure, each data set corresponding to each individual frequency was used to identify one set of parameters. This meant all operating frequencies would give a unique set of parameters.

One of the important things to note during system identification is that since two derivative terms were applied in the identification procedure, the noise aspect has to be addressed properly. It is important to pass the signal output of the derivative term through a filter to negate the impacts of high frequency noise. However, this filter usually introduces a phase shift which could lead to further errors. To minimize the phase shift introduced by the lowpass filters, the signals were passed through a zero-phase filter. It is the process of filtering the given signal in both forward and reverse directions as shown in FIG. 22.

The result has the following characteristics zero-phase distortion as shown in FIGS. 22A and 22B.

3.2 Model Parameter Identification

A model is a mathematical representation of a physical, biological or information system. Models allow us to reason about a system and make a prediction about how a system behaves. A dynamical system is one in which the effects of actions do not occur immediately. The differential equation describing the dynamics of the probe is as, follows.

$$K_T i = J \frac{d^2\theta}{dt^2} + B \frac{d\theta}{dt} + K\theta \quad \quad 3.1$$

or, $$i = \frac{J}{K_T} \frac{d^2\theta}{dt^2} + \frac{B}{K_T} \frac{d\theta}{dt} + \frac{K}{K_T} \theta \quad \quad 3.2$$

Where, J is the moment of inertia, B is the friction coefficient, K is the spring constant, $K_T$ is the torque constant, i is the current through the coils, θ is the angle made by the oscillating beam.

It is important to understand that no matter how careful one is in selecting the form of the assumed system model, it will never be an exact representation of the system. The experimental data will not be consistent with the assumed model for any value of the actual parameters. The model might be very close, but it will not be exact as the measurements of the response will always be made with real and hence imperfect instruments. Grey box modeling was chosen to retain the concept of an assumed model structure in order to reduce the scope of the problem, yet avoid the inflexibility of requiring that the model exactly reproduce the experimental data [5]. The assumed model structure includes the essential characteristics of the true system as validated by the low error index values. This selection of the model above is the probably most significant engineering decision in system identification. We need to estimate the best fit parameters that meet the required error criterion. The approach to parameter estimation is to minimize the error between the model response and the actual measured response, using a least squares criterion.

The model equation in 3.1 can be written in a matrix form, $$\begin{bmatrix} \frac{d^2\theta}{dt^2} & \frac{d\theta}{dt} & \theta \end{bmatrix} \cdot \begin{bmatrix} \frac{J}{K_T} \\ \frac{B}{K_T} \\ \frac{K}{K_T} \end{bmatrix} = [i] \quad \quad 3.3$$

Let $x(t_k) = \begin{bmatrix} \frac{d^2\theta}{dt^2}(t_k) & \frac{d\theta}{dt}(t_k) & \theta(t_k) \end{bmatrix}$ and $y = [i(t_k)]$ be the signals at a particular time point($t_k$). Equation 3.3 can be written as $$x(t_k) \cdot K = y(t_k) \quad \quad 3.4$$

where, $K = \begin{bmatrix} \dfrac{J}{K_T} & \dfrac{B}{K_T} & \dfrac{K}{K_T} \end{bmatrix}^T$.

Now, arranging N samples of θ and i in a matrix form, $$X \cdot K = Y \text{ where, } X = \begin{bmatrix} \dfrac{d^2\theta(t_1)}{dt^2} & \dfrac{d\theta(t_1)}{dt} & \theta(t_1) \\ \dfrac{d^2\theta(t_2)}{dt^2} & \dfrac{d\theta(t_2)}{dt} & \theta(t_2) \\ \vdots & \vdots & \vdots \\ \dfrac{d^2\theta(t_N)}{dt^2} & \dfrac{d\theta(t_N)}{dt} & \theta(t_N) \end{bmatrix} \text{ and } Y = \begin{bmatrix} i(t_1) \\ i(t_2) \\ \vdots \\ i(t_N) \end{bmatrix} \quad 3.5$$

The optimal estimates of K, defined as $\hat{K}$, can be determined by least squares fit of the experimental data to the model as [7]

$$\hat{K} = (X^T \cdot X)^{-1} \cdot X^T \cdot \hat{Y} \quad \quad 3.6$$

The goal here is to find the optimum parameter set K that provides the best fit for all N samples of data within a certain error criterion. This is accomplished by doing a linear fit of the data samples. Linear regression is the method used to model linear relationship between dependent variable and one or more independent variables. It is based on the least squares principle, that is, the model is fit such that the sum of squares of differences of observed and predicted values is minimized. Let $e = Y - \hat{Y}$ be the difference between the experimental data and the predicted data with the chosen parameter set, $$e = Y - X \cdot \hat{K} \quad \quad 3.7$$

This model above expresses the value of a dependent variable as a linear function of one or more independent variables. The error or the residual thus measures the closeness of fit of the predicted values and actual values. A normalized error index, defined by, $$E_I = \sqrt{\dfrac{\sum_{i=1}^{N}(Y(t_i) - \hat{Y}(t_i))^2}{\sum_{i=1}^{N}(Y(t_i))^2}} \cdot 100\% \quad \quad 3.10$$

was used to quantify the model accuracy, in which $Y(t_i)$ was the $i_{th}$ measurement, $\hat{Y}(t_i)$ was the prediction of $Y(t_i)$ and N is the total number of data points used.

This test yielded an error index of less than 5%, which was indicative of positive verification that the model was able to characterize the response of the beam in response to the current reference. With $$C_1 = \dfrac{J}{K_T}, C_2 = \dfrac{B}{K_T}, C_3 = \dfrac{K}{K_T}$$

defined, Table 2 shows the corresponding best fit parameter estimates and the corresponding error index.

TABLE 2

Best fit parameter estimates

| Frequency (Hz) | C1 | C2 | C3 | Error Index $E_I$ (%) |
|---|---|---|---|---|
| 8 | 6.89E−06 | 8.25E−05 | 8.12E−02 | 4.62 |
| 9 | 6.04E−06 | 8.29E−05 | 8.23E−02 | 3.25 |
| 10 | 5.02E−06 | 8.17E−05 | 8.15E−02 | 3.19 |
| 11 | 4.07E−06 | 7.85E−05 | 7.77E−02 | 6.26 |
| 12 | 3.56E−06 | 8.08E−05 | 7.89E−02 | 2.83 |
| 13 | 2.82E−06 | 7.80E−05 | 7.55E−02 | 1.92 |
| 14 | 1.76E−06 | 7.04E−05 | 6.79E−02 | 1.46 |
| 15 | 2.30E−06 | 7.46E−05 | 7.20E−02 | 1.48 |

Chapter 4: Controller Design

Controller design is a rich problem where many factors need to be considered. Typical requirements are that load disturbances should be minimized, the controller should inject only a moderate amount of measurement noise, the output should follow variations in the command signal well and the closed loop system should be insensitive to process variations.

In order to obtain design the optimum controller that meets the system performance specifications in terms of maximum overshoot and settling time, pole placement method was used. Following is the method used for controller design using pole placement approach (also known as polynomial approach) which is the most straightforward way to designing a controller.

Figure 4:
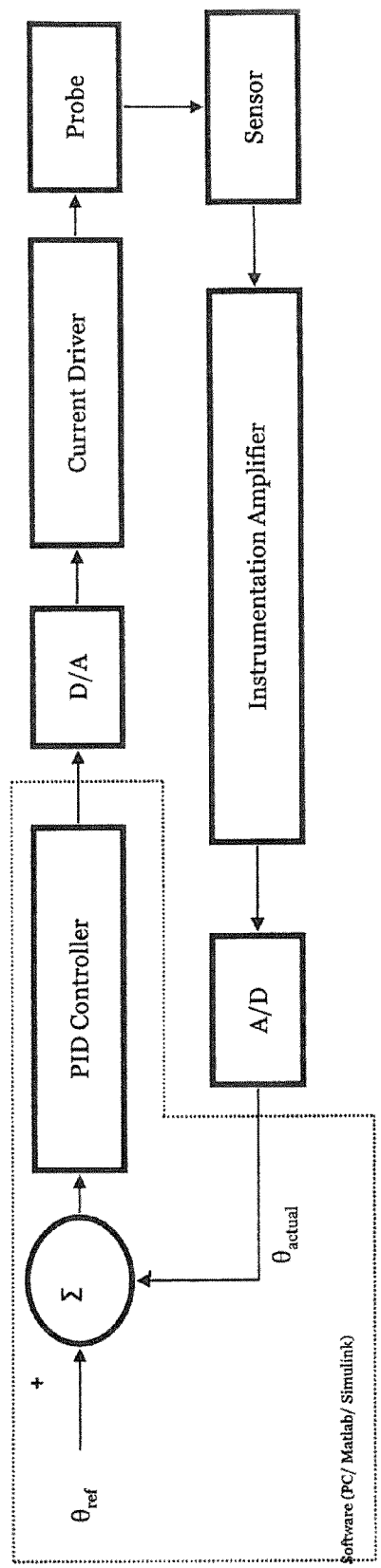
FIG. 4 shows a system block diagram.

The design started with an assumption of what form the controller must take in order to control the given plant. For the system, a PID configuration, as shown in FIG. 4.1 was chosen. PID Controller is a very common way of using feedback in engineering system in which the control signal for the system is formed entirely from the error signal. The command signal is called the reference signal. The input output relation for an ideal PID controller with error feedback is $$u = K_P \cdot e + K_I \cdot \int_0^t e(\tau) \cdot d\tau + K_D \cdot \dfrac{de}{dt} \quad \quad 4.1$$

where e is the difference between the reference signal and the actual signal, u is the control signal generated by the controller, $K_P$ is the proportional gain, $K_I$ is the integral gain and $K_D$ is the derivative gain.

The control action in a PID controller is the sum of three terms: proportional feedback, the integral term and derivative action. From that assumption a symbolic characteristic equation was formed (Equation 4.2). Hence, the transfer function of the controller is $$G_c(s) = \dfrac{U(s)}{E(s)} = K_D s + K_P + \dfrac{K_I}{s} \quad \quad 4.2$$

The transfer function G(s) of the probe can be expressed as $$G(s) = \dfrac{\theta(s)}{U(s)} = \dfrac{1}{C_1 \cdot s^2 + C_2 \cdot s + C_3} \quad \quad 4.3$$

where, $C_1 = \dfrac{J}{K_T}, C_2 = \dfrac{B}{K_T}, C_3 = \dfrac{K}{K_T}$

If the sensor dynamics is negligible, FIG. 23 can be simplified as shown in FIG. 24

FIG. 4.2: Closed Loop System Block Diagram with Appropriate Transfer Functions

The transfer function of the closed-loop system is $$G(s)_{C.L} = \frac{\theta(s)}{\theta_{REF}(s)} = \frac{G_c(s) \cdot G(s)}{1 + G_c(s) \cdot G(s)} = \frac{\frac{K_D}{C_1}s^2 + \frac{K_P}{C_1}s + \frac{K_I}{C_1}}{s^3 + \left(\frac{C_2 + K_D}{C_1}\right)s^2 + \left(\frac{C_3 + K_P}{C_1}\right)s + \frac{K_I}{C_1}} \quad 4.4$$

Based on the standard second order system approximation, $$H(s) = \frac{\omega_n^2}{s^2 + 2\xi\omega_n s + \omega_n^2} \quad 4.5$$

where, $\omega_n$ is the natural frequency of the system and $\xi$ is the damping ratio ($0 \le \xi \le 1$). These values are determined from the maximum overshoot $$\left(e^{\frac{-\pi\xi}{\sqrt{1-\xi^2}}} \cdot 100\%\right)$$

and settling time $$\left(\frac{4}{\xi \cdot \omega_n} \text{ for 2\% criterion}\right)$$

requirements. The dominant poles for the closed loop system are $$P_{1,2} = -\omega_n \xi \pm j\omega_n \sqrt{1-\xi^2} \quad 4.6$$

Selecting a pole ten times the magnitude of the dominant poles, the non-dominant pole is $$P_3 = 10|-\omega_n \xi + j\omega_n \sqrt{1-\xi^2}| \quad 4.7$$

The third order closed loop transfer function based on the dominant and non-dominant poles is obtained as $$G_{CL}(s) = \frac{1}{(s-P_1) \cdot (s-P_2) \cdot (s-P_3)} = \frac{1}{s^3 - (P_1 + P_2 + P_3)s^2 + (P_1P_2 + P_2P_3 + P_1P_3)s - P_1P_2P_3}$$

Further simplification gives $$G_{CL}(s) = \frac{1}{s^3 + K_2 \cdot s^2 + K_1 \cdot s + K_0} \quad 4.8$$

Where, $K_2 = -(P_1 + P_2 + P_3)$ $K_1 = P_1P_2 + P_2P_3 + P_1P_3$ $K_0 = -P_1P_2P_3$ Equating denominator of 4.4 to 4.8, the controller gains are calculated as, $$K_D = K_2 \cdot C_1 - C_2 \quad 4.9$$

$$K_P = K_1 \cdot C_1 - C_3 \quad 4.10$$

$$K_I = K_0 \cdot C_1 \quad 4.11$$

Based on closed loop transfer function of the system, there are additional finite zeros that can introduce additional overshoot. In order to restore a 'poles only' response, a pre-filter (F(s) in 4.12) that cancels the unwanted zeros is added.

$$F(s) = \frac{K_I}{K_D s^2 + K_P s + K_I}. \quad 4.12$$

The pre-filter is added between the reference and the summing junction (shown in FIG. 24.

The designed controller represents an idealized controller but several considerations have to be made to make the controller practical, foremost of which is to account for possible system nonlinearities. Linear models help one understand and simplify many aspects of the control system. However, there are several nonlinear phenomena that must be taken into consideration, such as limitations on the input current, the position output of the probe and so on. For this system which operates over a wide range of conditions of frequency and current, it may happen that the control variable reaches the actuator limits. When this happens, the feedback loop is broken and the system runs in open loop because the actuator remains at its limit independently of the process output. The integral gain and the controller output could potentially become very large due to which the control signal would remain saturated. This results in large transients and is known as integrator windup. In order to reduce the effects of possible integrator windup, the system was tested and verified to prevent from going into saturation in normal operating conditions.

PID controller is the controller of choice as it possesses all the necessary characteristics to meet the system specifications such as fast reaction on change of the controller input, increase in control signal to lead error towards zero and suitable action inside control error area to eliminate oscillations. Derivative mode improves stability of the system and enables increase in gain and decrease in integral time constant, which increases speed of the controller response. However, there are practical issues that need to be considered when implementing the PID controller. A drawback with derivative action is that an ideal derivate has high gain for high frequency signals which means that the high frequency measurement noise generates large variations in the control signal.

Proportional control always gives steady state error. The error will decrease with increasing gain, but the tendency towards oscillation will also increase. The strength of integral action increases with decreasing integral time. The steady state error declines when integral action is used. The tendency for oscillation also increases with decreasing integral time. Damping increases with increasing derivative time, but decreases again when derivative time becomes too large. The derivative action can be interpreted as providing prediction by linear extrapolation. This implies that the derivative action does not help if the prediction time is too large. Also, the period of oscillation increases when derivative time is increased. The effect of tuning the control gains are summarized in Table 4.1.

TABLE 3

Effect of manual tuning of the controller gains

| Parameter | Speed of response | Stability | Accuracy |
|---|---|---|---|
| increasing K | increases | deteriorate | improves |
| increasing $K_i$ | decreases | deteriorate | improves |
| increasing $K_d$ | increases | improves | no impact |

There are however, some practical considerations that have to be made when implementing the PID Controller. Although many aspects of a control system is understood based on linear theory, some nonlinear effects must also be accounted. Windup is a phenomenon, which is caused by the interaction of integral action and saturations. All actuators have limitations and so does the probe mechanism. One can only send in so much current into the coils to not heat the space around the coil as well as to consume less power for a wide range of operating conditions. It thus may happen that the control variable reaches the actuator limits. If ever this were to happen, the feedback loop gets broken and the system runs as an open loop because the actuator stays at its limit independently of the process output. In the controller that is using an integral portion, the error will continue to be integrated. This means that the integral term may become very large and 'wind up'. If an integral wind up arises, then it becomes necessary to negate the error sign for a long period to bring the system back to normal. In order to avoid this situation, the operating ranges of the system should be set lower levels than the maximum capacity of the system, mainly in terms of the current specifications. This is implemented in software by using saturation limit blocks to avoid the control signal getting too large. This consideration is especially important as high control gains could lead to actuator breakdowns and could pose serious injury risks to the user. Using the steps described above, the appropriate control gains were calculated which are tabulated in Table 4.

TABLE 4

Control gains for the operating frequency range

| Frequency (Hz) | Maximum Overshoot (%) | Settling Time (s) | Kp | Kd | Ki |
|---|---|---|---|---|---|
| 8 | 10 | 0.060 | 1.042 | 0.009 | 98.771 |
| 9 | 10 | 0.055 | 1.089 | 0.008 | 112.392 |
| 10 | 10 | 0.050 | 1.096 | 0.008 | 124.316 |
| 11 | 10 | 0.045 | 1.103 | 0.007 | 138.482 |
| 12 | 10 | 0.040 | 1.228 | 0.007 | 172.419 |
| 13 | 10 | 0.035 | 1.274 | 0.006 | 203.457 |
| 14 | 10 | 0.035 | 0.773 | 0.004 | 126.810 |
| 15 | 10 | 0.300 | 1.431 | 0.006 | 264.410 |

Chapter 5: System Performance

There are two aspects to analyzing the performance of the system designed. First, detailed analysis had to be carried out in software to avoid the risk of running into actuator limits and so on. Only after observing satisfactory performance in software, the system would be tested in hardware. Because of the low error index values (Chapter 3), it was assumed that the performance in software and in hardware should ideally be similar. However, there are usually differences in how the system performs in simulation and in the actual hardware and proper precautions should be taken, especially to make sure that the controller does not wind up, mostly because of disturbances.

The performance of the closed loop system was characterized by closely analyzing the performance graph by calculating the difference between the reference signal and the output position signal on a point to point basis to find out the maximum difference between the two. Also FFT comparison was made between the reference signal, the signal after the pre-filter and the position signal to make sure that the position signal did in fact have the same frequency spectrum as the reference signal (shown in FIG. 25D). Based on the implementation of the closed loop system, the system performed very well for the entire frequency range. The maximum error between the reference signal and the actual signal at any instant was less than 0.5° for all frequencies (shown in FIG. 25C). This was also demonstrated in the closed loop step response where there was minimal overshoot and the settling time was within the time specified (shown in FIG. 25B). When compared to the open loop response which had a lot of more than 80% and steady state error (both shown in FIG. 25A), the usage of a feedback mechanism to improve performance was duly justified. In the process of getting the desired performance, the current levels reached a maximum to 0.8 A, which is below safe operating range of the current driver circuit. C Chapter 6: Conclusion The concept of a feedback controlled mechanical sector scanner based on the tuning fork model was proven. A conventional control system was designed and implemented in software to accomplish a feedback controlled ophthalmic ultrasonic apparatus with a tuning fork-type oscillator. The model parameters for the custom built prototype were estimated with high accuracy (less than 5%) and a PID controller was used to provide the appropriate control gains to meet the system performance specifications. System identification was accomplished in an iterative manner and unique parameter sets were estimated for each individual frequency because of the physical differences in probe behavior on different frequencies. A high current capacity power circuit was designed to supply energy for the oscillations.

Identification of the model parameters of the system for the entire operating frequency range was necessary in order to design a robust performing controller. A grey-box approach was used since the beam behavior was theoretically analyzed as typical mass spring scenario. The model parameters were discovered using experimental data and least squares curve fitting approach. The input to the model was current and the output was the beam angle. Initial experiments to obtain a single set of parameters for all frequencies resulted in large error index values.

Figure 27A:
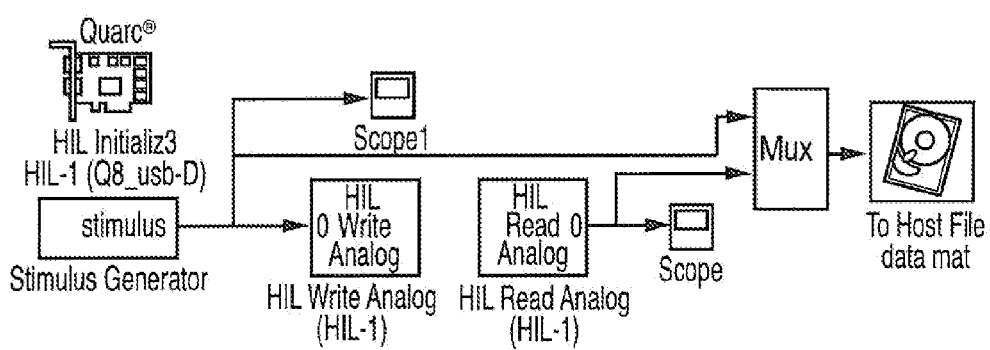
Figure 27C:
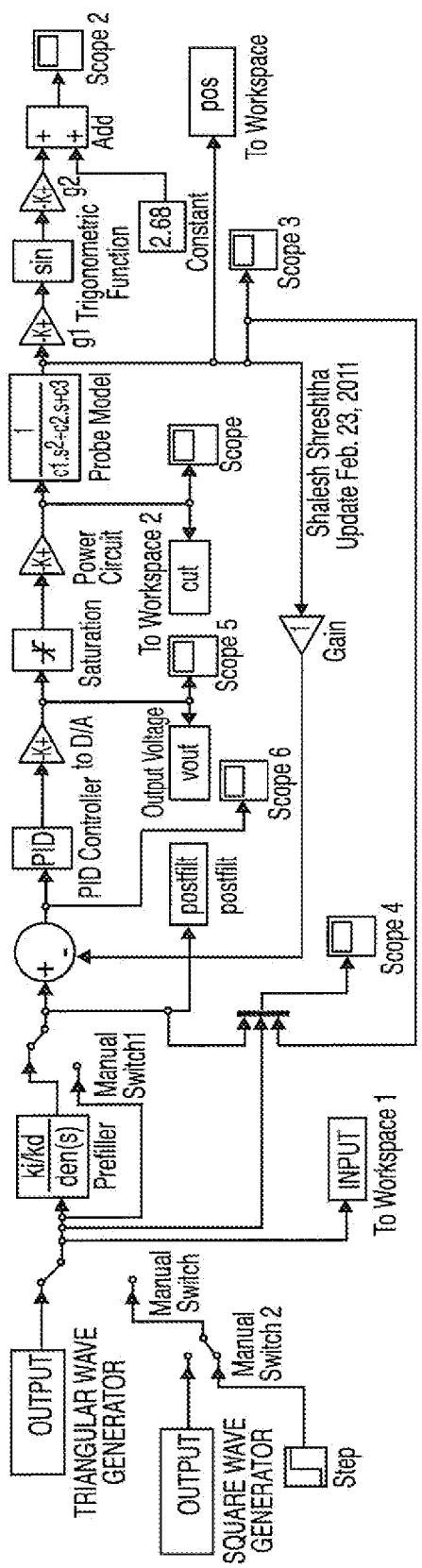
Figure 27D:
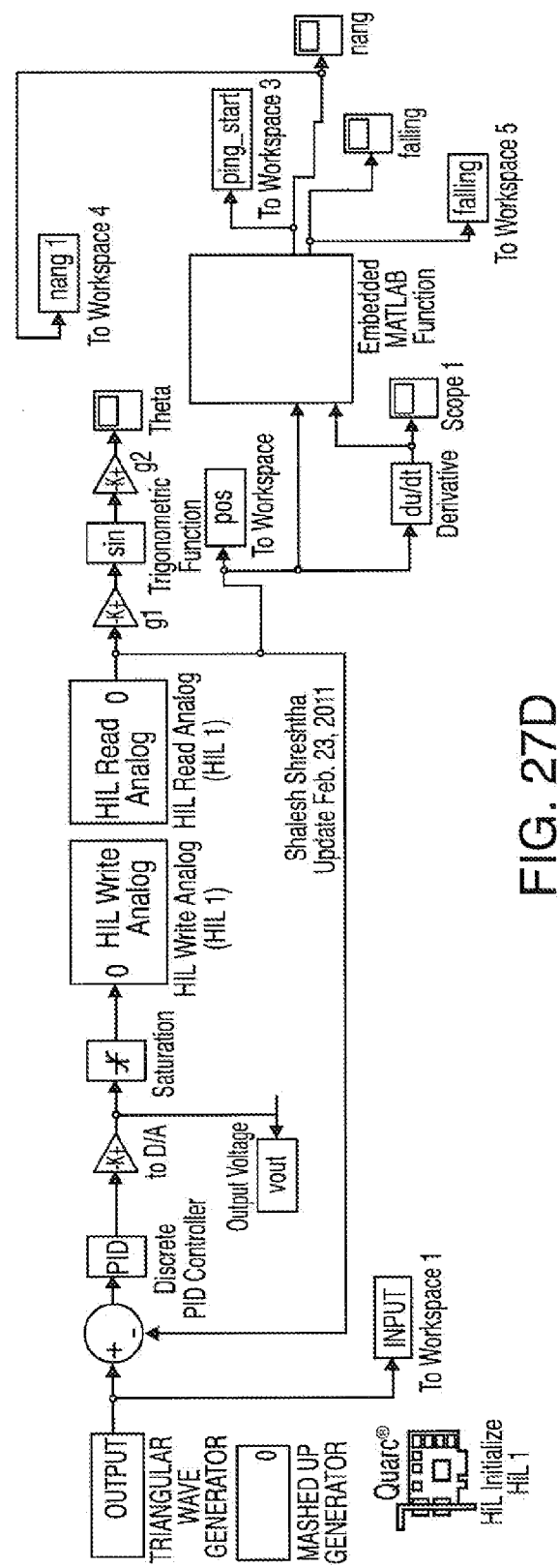

FIGS. 27A-27D show details of the equipment used to simulate a transducer in accordance with the present invention and FIG. 27E shows a program listing for the simulation.

Numerous modifications may be made to this invention without departing from its scope as defined in the appended claims.

We claim:

1. An ultrasonic transducer device for performing an optical scan on the eye of a patient comprising:
 a frame;
 a sonic transducer generating waves;
 a main beam having a free end supporting said sonic transducer and a support point opposite said free end, said support point being secured to said frame; and
 a driving mechanism disposed between said free end and said support point and driving said main beam in a reciprocating angular motion
 said sonic transducer being adapted to direct said waves at the patient's eye as said sonic transducer is being reciprocated on said main beam to scan the patient's eye.

2. The device of claim 1 wherein said driving mechanism includes a first electromagnetic coil disposed on one side of the main beam and a second electromagnetic coil disposed on a second side of the main beam and a controller generating respective currents for said first and second electromagnetic coils to selectively deflect said main beam between said coils.

3. The device of claim 1 further comprising a counterbalancing beam oscillating in a manner selected to counterbalance the movement of said main beam to reduce oscillations.

4. A diagnostic apparatus for treating an eye of a patient, said apparatus comprising:
- a stationary frame;
- a beam having a fixed end and a free end, said fixed end being attached to and cantileveredly supported by said frame;
- an ultrasonic sensor disposed at said free end and configured to generate selectively sound waves for directing to the eye;
- a magnet attached the beam;
- a first electromagnetic coil supported on the frame adjacent to said magnet; and
- a controller configured to energize said electronic magnet to move said beam in a predetermined direction.

5. The diagnostic apparatus of claim 4 comprising a second electromagnetic coil energized by said controller, said first and second electromagnetic coils flex said beam in a reciprocating motion.

6. The diagnostic apparatus of claim 4 further comprising a sensor arranged to determine the position of said beam, said sensor generating sensing signals provided to said controller.

\* \* \* \* \*